United States Patent
O'Connell

(12) 
(10) Patent No.: US 6,517,559 B1
(45) Date of Patent: Feb. 11, 2003

(54) BLOOD FILTER AND METHOD FOR TREATING VASCULAR DISEASE

(76) Inventor: Paul T. O'Connell, 2414 Harrison St., Evanston, IL (US) 60201

(*) Notice: Subject to any disclaimer, the term of this patent is extended or adjusted under 35 U.S.C. 154(b) by 0 days.

(21) Appl. No.: 09/564,141

(22) Filed: May 3, 2000

Related U.S. Application Data

(63) Continuation-in-part of application No. 09/304,111, filed on May 3, 1999, now Pat. No. 6,267,776.

(51) Int. Cl.$^7$ .............................................. A61B 17/00
(52) U.S. Cl. ........................ 606/158; 606/108; 606/200
(58) Field of Search .................................. 606/200, 159, 606/108, 192, 194, 191; 623/1.15–1.22

(56) References Cited

U.S. PATENT DOCUMENTS

| | | |
|---|---|---|
| 2,281,448 A | 4/1942 | Mathey |
| 3,334,629 A | 8/1967 | Cohn |
| 3,540,431 A | 11/1970 | Mobin-Uddin |
| 3,868,956 A | 3/1975 | Alfidi et al. |
| 3,952,747 A | 4/1976 | Kimmell, Jr. |
| 4,425,908 A | 1/1984 | Simon |
| 4,494,531 A | 1/1985 | Gianturco |
| 4,643,184 A | 2/1987 | Mobin-Uddin |
| 4,657,543 A | 4/1987 | Langer et al. .............. 604/891 |
| 4,688,553 A | 8/1987 | Metals |
| 4,727,873 A | 3/1988 | Mobin-Uddin |
| 4,781,177 A | 11/1988 | Lebigot |
| 4,817,600 A | 4/1989 | Herms et al. |
| 4,873,978 A | 10/1989 | Ginsburg |
| 4,990,156 A | 2/1991 | Lefebvre ..................... 606/200 |
| 5,059,205 A | 10/1991 | El-Nounou et al. ......... 606/200 |
| 5,108,418 A | 4/1992 | Lefebvre ..................... 606/200 |
| 5,133,733 A | 7/1992 | Rasmussen et al. ........ 606/200 |
| 5,152,777 A | 10/1992 | Goldberg et al. ........... 606/200 |
| 5,242,462 A | 9/1993 | El-Nounou et al. ......... 606/200 |
| 5,324,304 A | 6/1994 | Rasmussen .................. 606/200 |
| 5,344,427 A | 9/1994 | Cottenceau et al. ........ 606/200 |
| 5,370,657 A | 12/1994 | Irie ............................. 606/200 |
| 5,375,612 A | 12/1994 | Cottenceau et al. ........ 128/899 |
| 5,383,887 A | 1/1995 | Nadal ......................... 606/200 |
| 5,415,630 A | 5/1995 | Gory et al. ................... 604/53 |
| 5,443,478 A | 8/1995 | Purdy ......................... 606/200 |
| 5,484,424 A | 1/1996 | Cottenceau et al. ........ 604/282 |
| 5,514,154 A | 5/1996 | Lau et al. .................... 606/195 |
| 5,527,338 A | 6/1996 | Purdy ......................... 606/200 |

(List continued on next page.)

FOREIGN PATENT DOCUMENTS

| | | | |
|---|---|---|---|
| EP | 0 809 981 A1 | 3/1997 | |
| WO | WO 00/49970 | 8/2000 | ............. A61F/2/01 |

OTHER PUBLICATIONS

Crochet et al., *Vena Tech–LGM filter: Long Term Results of a Prospective Study*, Radiology, 1993, vol. 188, pp. 857–860.

Murphy et al., *LGM Vena Cava Filter: Objective Evaluation of Early Results*, Journal of Vascular and Interventional Radiology, 1991, vol. 2, pp. 107–115.

(List continued on next page.)

*Primary Examiner*—Olik Chaudhuri
*Assistant Examiner*—(Vikki) Hoa B. Trinh
(74) *Attorney, Agent, or Firm*—Marshall, Gerstein & Borun

(57) ABSTRACT

A filter is provided that is convertible from a filter configuration to an open, stent-like configuration. The filter includes a plurality of intraluminal filter elements (filter legs) that may be formed into a single cone or dual cone filter structure. A retainer secures the filter legs in the filter configuration upon initial deployment within a vessel. The retainer is then either self-releasing or removable to permit the filter legs to expand from the filter configuration into what may generally be described as an open or stent-like configuration. A filter web extends, at least in part, between the filter legs.

27 Claims, 9 Drawing Sheets

U.S. PATENT DOCUMENTS

| | | | |
|---|---|---|---|
| 5,540,680 A | 7/1996 | Guglielmi et al. | 606/32 |
| 5,601,595 A | 2/1997 | Smith | 606/200 |
| 5,618,563 A | 4/1997 | Berde et al. | 424/501 |
| 5,624,449 A | 4/1997 | Pham et al. | 606/108 |
| 5,626,605 A | 5/1997 | Irie et al. | 606/200 |
| 5,630,801 A | 5/1997 | Roussigne et al. | 604/95 |
| 5,634,942 A | 6/1997 | Chevillon et al. | 623/1 |
| 5,669,905 A | 9/1997 | Scheldrup et al. | 606/32 |
| 5,670,161 A | 9/1997 | Healy et al. | 424/426 |
| 5,693,067 A | 12/1997 | Purdy | 606/200 |
| 5,713,853 A | 2/1998 | Clark et al. | 604/53 |
| 5,725,550 A | 3/1998 | Nadal | 606/200 |
| 5,743,905 A | 4/1998 | Eder et al. | 606/32 |
| 5,746,767 A | 5/1998 | Smith | 606/200 |
| 5,755,790 A | 5/1998 | Chevillon et al. | 623/12 |
| 5,800,457 A | 9/1998 | Gelbfish | 606/200 |
| 5,810,874 A | 9/1998 | Lefebvre | 606/200 |
| 5,836,968 A | 11/1998 | Simon et al. | 606/200 |
| 5,836,969 A | 11/1998 | Kim et al. | 606/200 |
| 5,843,118 A | 12/1998 | Sepetka et al. | 606/194 |
| 5,853,420 A | 12/1998 | Chevillon et al. | 606/200 |
| 5,893,869 A | 4/1999 | Barnhart et al. | 606/200 |
| 6,042,598 A * | 3/2000 | Tsugita et al. | 606/200 |
| 6,267,776 B1 * | 7/2001 | O'Connell | 606/200 |

OTHER PUBLICATIONS

Taylor et al., *Vena Tech Vena Cava Filter: Experience and Early Follow–Up*, Journal of Vascular and Interventional Radiology, 1991, vol. 2, pp. 435–440.

Cull et al., *The Vena Tech Filter: Evaluation of a New Inferior Vena Cava Interruption Device*, The Journal of Cardiovascular Surgery, 1991, vols. 32–50, pp. 691–696.

Ricco et al., *Percutaneous Transvenous Caval Interruption with the "LGM" Filter: Early Results of a Multicenter Trial*, Annals of Vascular Surgery, 1988, vol. 3, 242–247.

Mohan et al., *Comparative Efficacy and Complications of Vena Caval Filters*, Journal of Vascular Surgery, 1995, vol. 21–20, pp. 235–246.

Ricco et al., *The LGM Vena Tech Caval Filter: Results of a Multicenter Study*, Annals of Vascular Surgery, 1995, vol. 59, pp. 89–100.

Grassi et al., *Vena Caval Occlusion After Simon Nitonol Filter Placement: Identification with MR Imaging in Patients with Malignancy*, JVIR, 1992, vol. 3, pp. 535–539.

Johnson et al., *CT of Greenfield Filters*, 16th Annual Meeting SCVIR, 1991, pp. 167.

Sweeny et al., *Deployment Problems with the Titanium Greenfield Filter*, JVIR, 1993, vol. 4, pp. 691–694.

Milward et al., *LGM (Vena Tech) Vena Caval Filter: Experience at a Single Institution*, JVIR, 1994, vol. 5, pp. 351–356.

Roehm et al., *The Bird's Nest Inferior Vena Cava Filter: Progress Report*, Radiology, 1988, vol. 168, pp. 745–749.

B. Braun Medical, Vena Tech Division, *A Patient's Guide to the Vena Tech LGM Vena Cava Filter*.

Coleman, *Overview of Interruption of the Inferior Vena Cava*, Seminars in Interventional Radiology, Sep. 1996, vol. 3, pp. 175–187.

Kraimps et al., *Conical Endocaval Filters with Metallic Struts: Search of a New Model*, Annals of Vascular Surgery, 1992, vol. 6, pp. 99–110.

Crochet et al., *Caval Incorporation of the LGM Vena Tech Filter: An Experimental Study*, JVIR, May–Jun. 1997, pp. 419, 425.

Simon et al., *Simon Nitonol Inferior Vena Cava Filter: Initial Clinical Experience*, Radiology, vol. 172, pp. 99–103.

Grassi, *Inferior Vena Caval Filters: Analysis of Five Currently Available Devices*, AJR, Apr. 1991, vol. 156, pp. 813–821.

Kraimps et al., *Optimal Central Trapping* (OPCETRA) *Vena Caval Filter: Results of Experimental Studies*, JVIR, Nov. 1992, pp. 697–701.

Dorfman, *Percutaneous Inferior Vena Caval Filters*, Radiology, 1990, vol. 174, pp. 987–992.

Greenfield et al., *Results of a Multicenter Study of the Modified Hook–Titanium Greenfield Filter*, Journal of Vascular Surgery, 1991, vol. 14, pp. 253–257.

Greenfield et al., *Twelve–Year Clinical Experience with the Greenfield Vena Caval Filter*, Surgery, Oct. 1998, pp. 706–712.

Wang et al., *Use of a Nitinol Gooseneck Snare to Open an Incompletely Expanded Over–the Wire Stainless Greenfield Filter*, AJR, Feb. 1999, vol. 172, pp. 499–500.

* cited by examiner

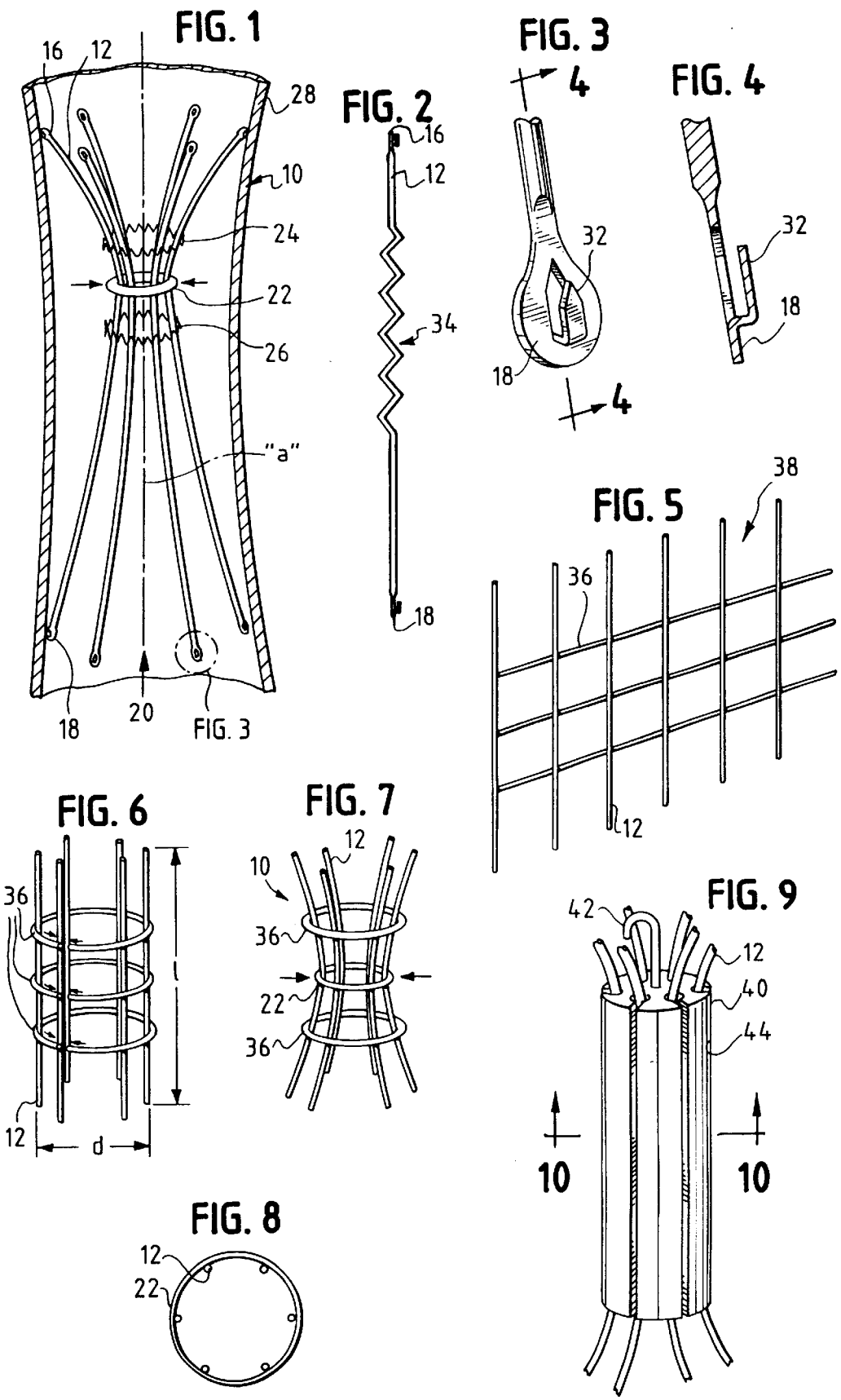

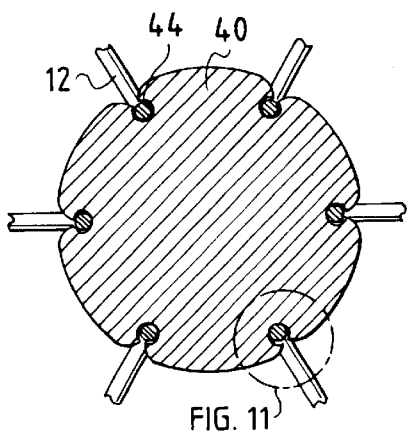
FIG. 10
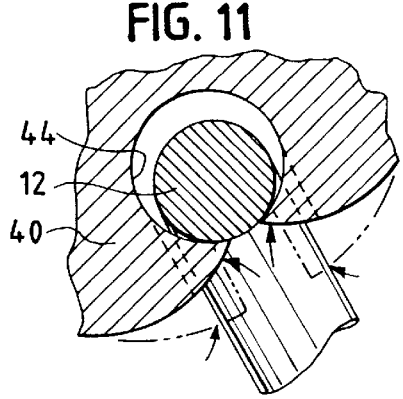
FIG. 11
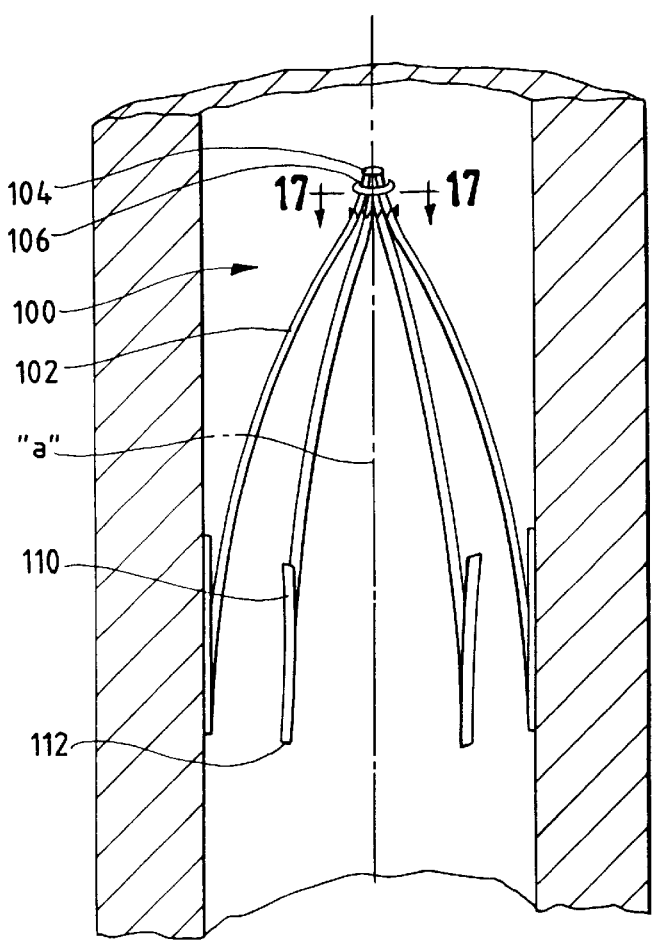
FIG. 12
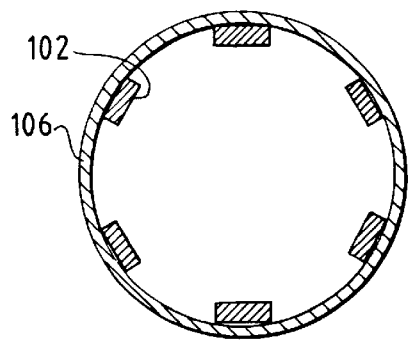
FIG. 13
FIG. 15
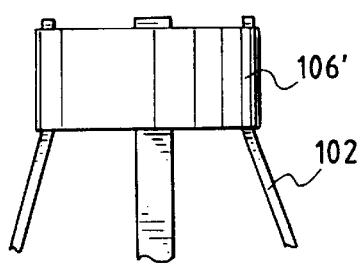
FIG. 14
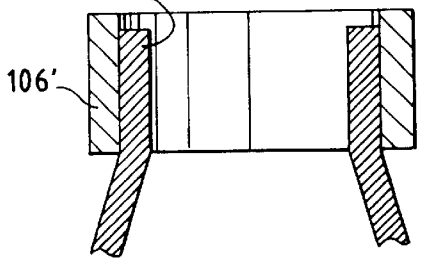
FIG. 16

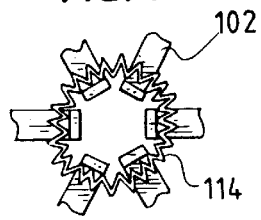
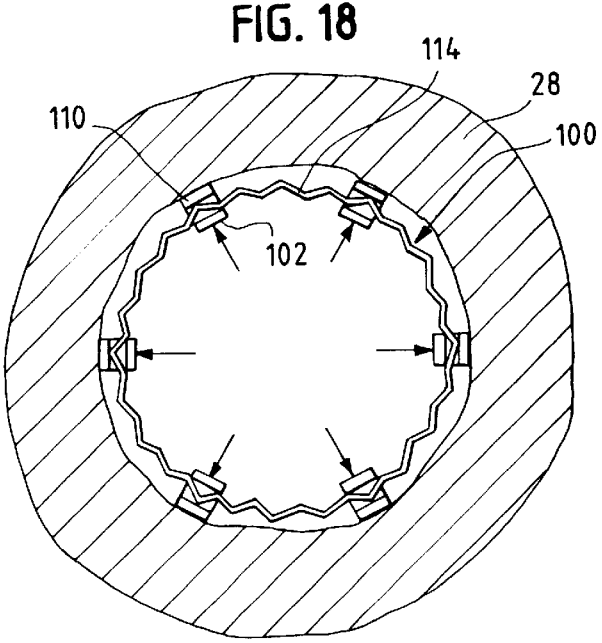
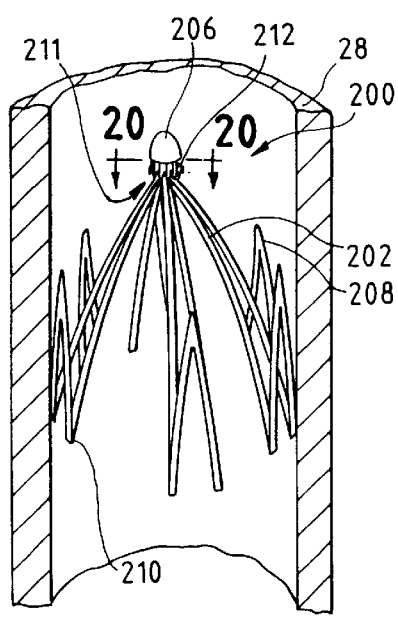
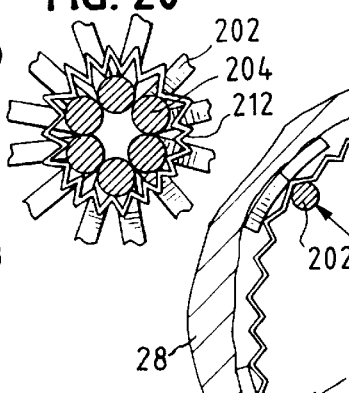
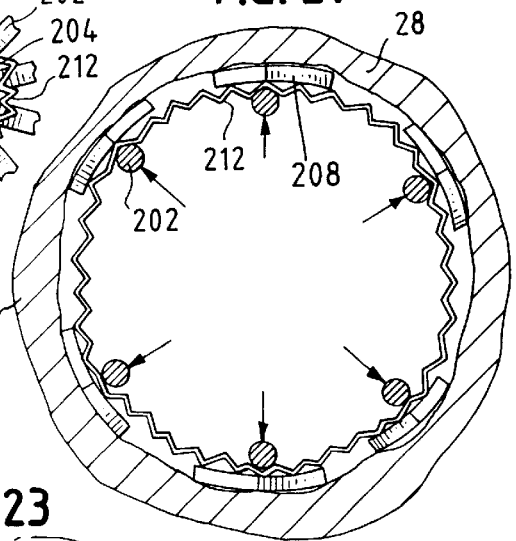
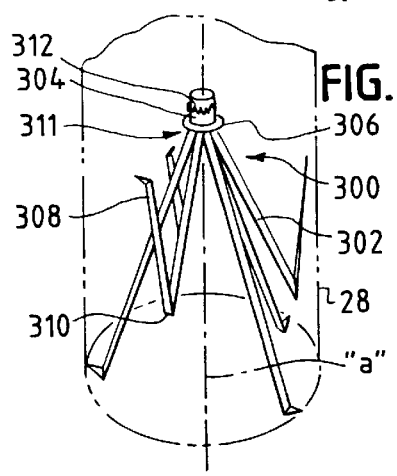
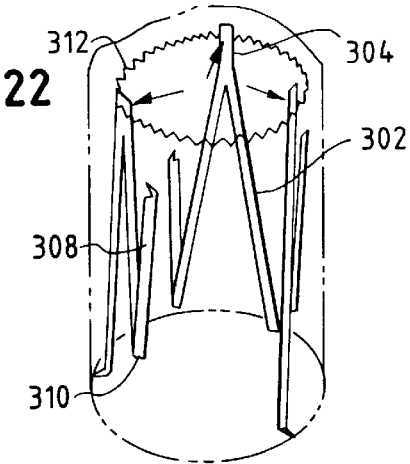

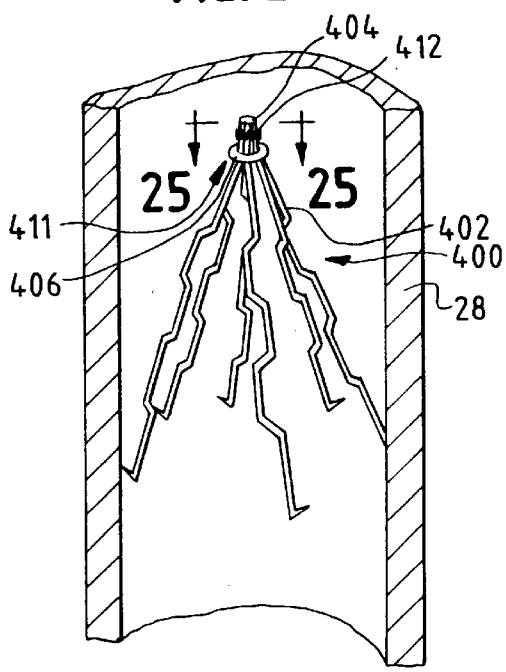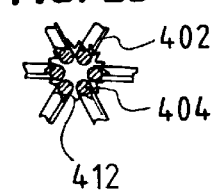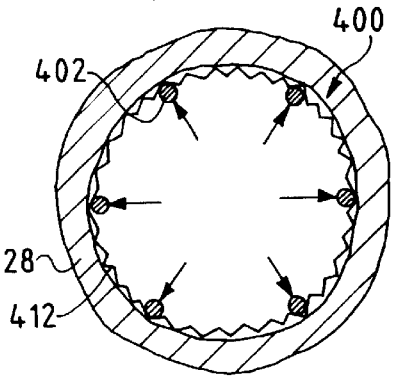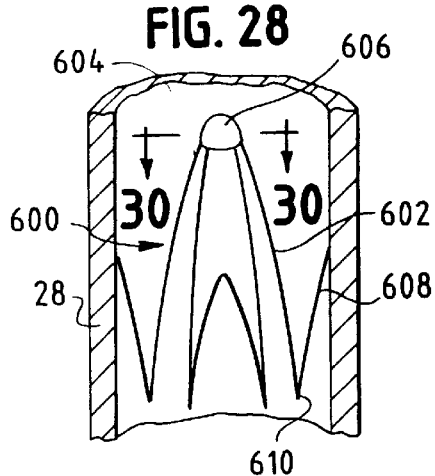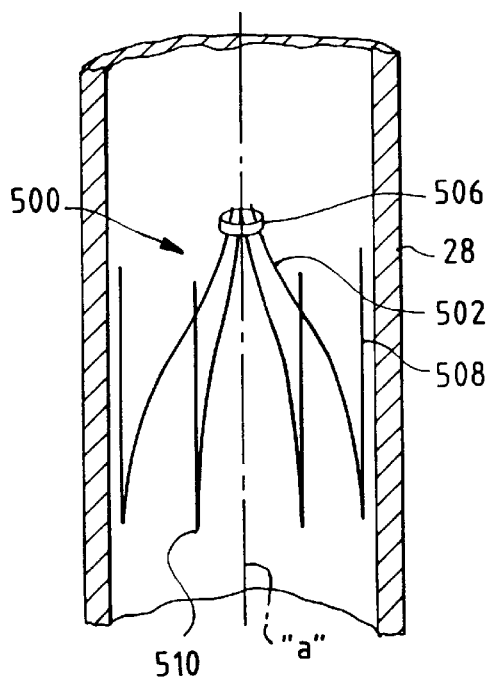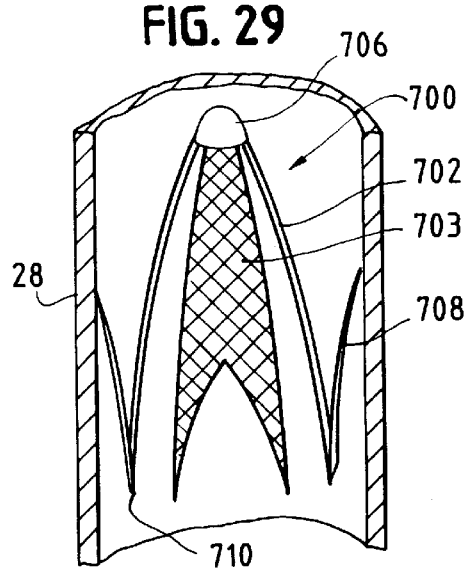

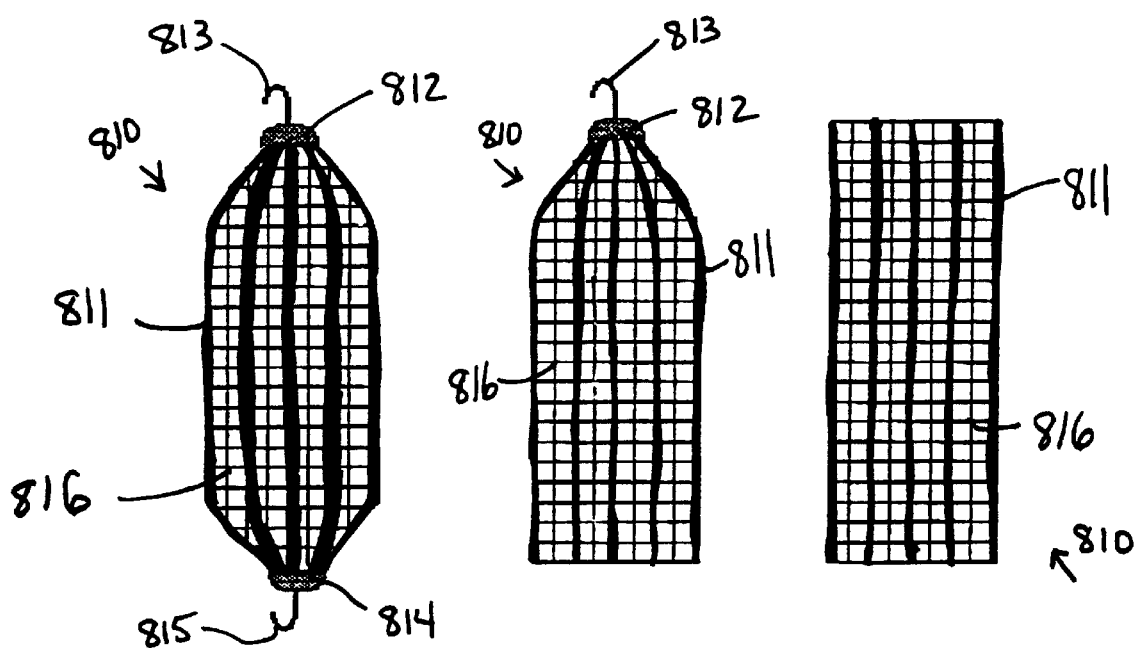

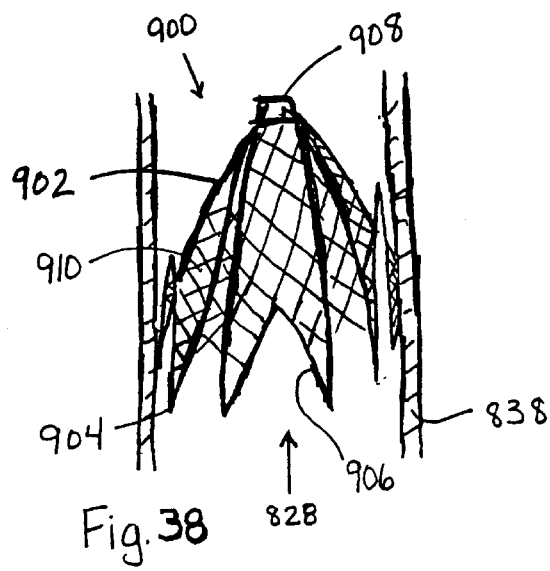
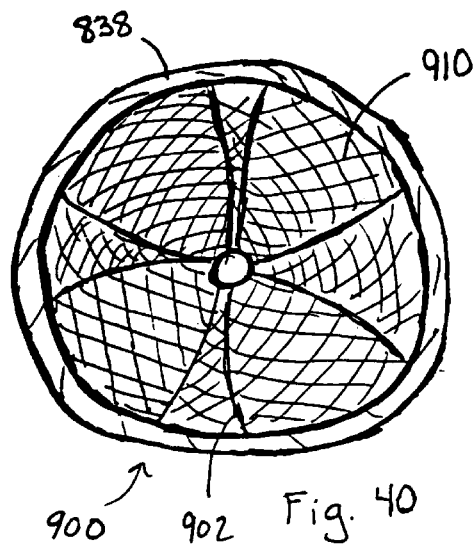
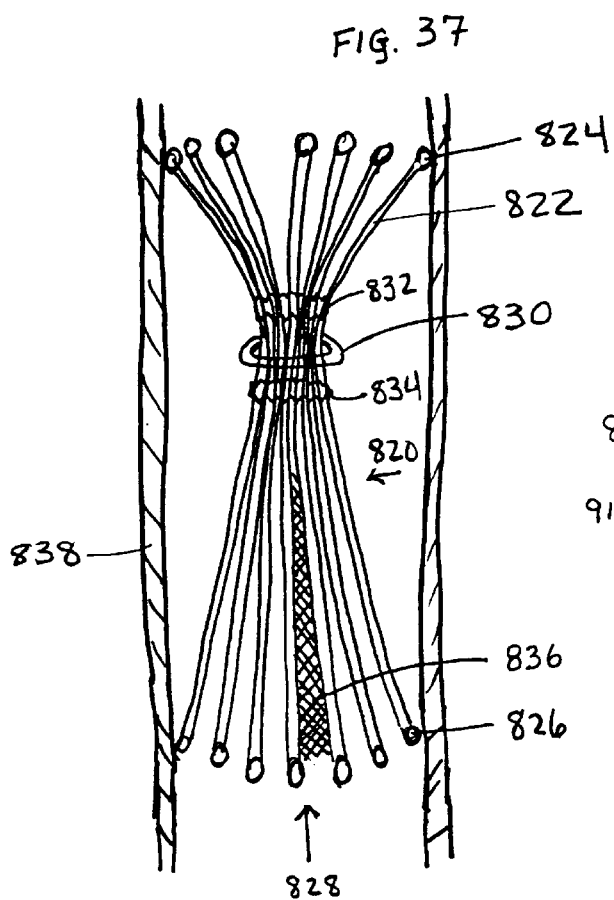
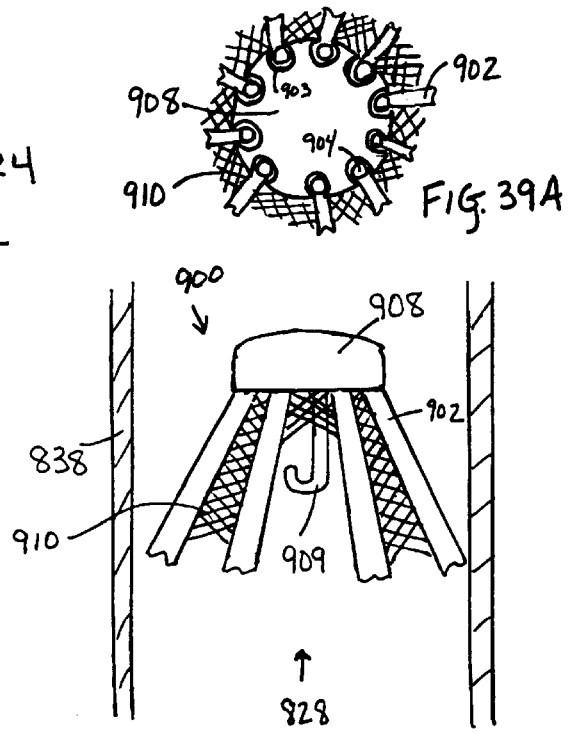
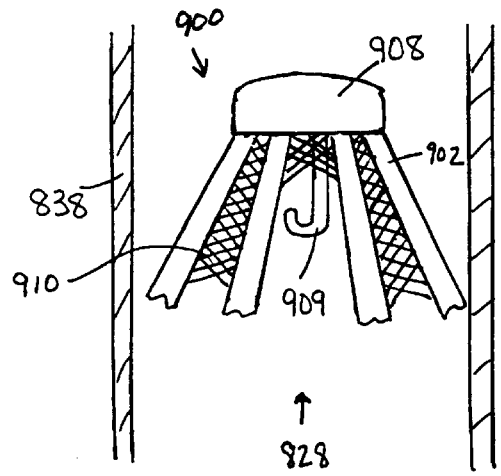

BLOOD FILTER AND METHOD FOR TREATING VASCULAR DISEASE

CROSS-REFERENCE TO RELATED APPLICATIONS

This application is a continuation-in-part of application of Ser. No. 09/304,111, filed May 3, 1999, now U.S. Pat. No. 6,267,776.

BACKGROUND OF THE INVENTION

1. Field of the Invention

The invention relates generally to devices for the treatment vascular disease and, more particularly, the invention relates to a filter device for placement within a blood vessel that is operable to catch and retain embolic material dislodged during the treatment of atherosclerotic disease.

2. Description of the Related Technology

Atherosclerotic disease in the coronary and carotid vasculature is one of the leading causes of morbidity and mortality in the United States. Atherosclerotic disease can cause insufficient circulation of oxygenated blood due to luminal narrowing caused by formation of atherosclerotic plaque. In addition, atherosclerotic disease can cause thromboembolism.

Atherosclerosis is a progressive, degenerative arterial disease that leads to occlusion of affected blood vessels, thereby reducing vessel patency, and hence, blood flow through them. During the course of this vascular disease, plaques develop on the inner lining of the arteries narrowing the lumen of the blood vessels. Sometimes these plaques become hardened by calcium deposits, resulting in a form of atherosclerosis called arteriosclerosis or "hardening of the arteries." Atherosclerosis attacks arteries throughout the body, but the most serious consequences involve damage to the vessels of the brain and heart. In the brain, atherosclerosis is the primary cause of strokes, whereas in the heart, when total blockage of an artery occurs, portions of heart muscle can die and disrupt the electrical impulses that make the heart beat.

The internal carotid artery is an artery often affected by atherosclerosis. When atherosclerosis is detected in the carotid artery, physicians need to remove the plaque, thereby restoring circulation to the brain and preventing a cerebral vascular accident.

Treatment for atherosclerosis ranges from preventive measures such as lowering fat intake and medication to endarterectomy, balloon angioplasty or atherectomy. In endarterectomy, the affected artery is surgically opened and plaque deposits are removed from the lining of the arterial wall. Occasionally during endarterectomy, large pieces of plaque break away from the arterial walls and enter the blood stream. Additionally, thrombotic material may develop if damage to the arterial wall occurs from the removal of plaque. Dislodged plaque deposits and thrombotic material, causing a condition called thromboembolism, may occlude smaller vessels downstream resulting in a vascular problems and potentially death. Thus, it is common practice by one skilled in the art to capture dislodged plaque, or any thrombotic material, by using a vacuuming procedure throughout the duration of the endarterectomy procedure. Although a significant percentage of plaque and thrombotic material is captured by this vacuuming procedure, pieces of plaque as well as thrombotic material inevitably escape.

Balloon angioplasty is a another method of treating atherosclerosis. In balloon angioplasty, a balloon-tipped catheter is inserted through the skin into the vessel and maneuvered to the lesion in the artery. The balloon tipped catheter is threaded through the lesion and inflated, increasing the vessel lumen to improve blood flow at the site. After deflating the balloon, stents are often inserted to keep the lumen of the vessel open, maintain blood flow and provide a scaffolding for tissue growth. Although balloon angioplasty and stenting are alternative methods of treatment, recent studies have documented adverse side effects associated with carotid stenting and, therefore, such procedures may not be as desirable as endarterectomy.

An additional method of treatment, atherectomy, is a procedure during which the plaque in coronary arteries is ground into minuscule particles that the body can clean from the bloodstream. Occasionally, during such procedures, large pieces of plaque break away from the arterial walls and enter the blood stream. As described above, this plaque debris can not be processed by the body and, therefore, must be vacuumed from the bloodstream to prevent the plaque from clogging arteries in the brain or elsewhere.

The primary use of blood filters historically has been to prevent pulmonary embolism. Blood filters are implanted within a vein, typically the inferior vena cava, and are intended to trap large blood clots while allowing blood to pass freely through the filter around the clot. In most cases trapped blood clots will normally dissolve over time.

Most often, blood filters are implanted within the inferior vena cava from a variety of peripheral vein access sites, for example, the jugular or femoral veins. An early example of such a filter was the Mobin-Uddin (MU) umbrella filter, which was developed and made available by American Edwards Laboratories in Santa Monica, Calif. in the 1970s. The Mobin-Uddin umbrella was composed of six flat ELGILOY spokes radiating from a hub and partially covered by a web designed to capture blood clots. MU filters were introduced into the body via a cutdown of the jugular or femoral vein and subsequent passing of a catheter through the access site to the filter implant site in the infrarenal inferior vena cava. While this method was an improvement over previous methods, the MU filter was associated with a high incidence of occlusion of the inferior vena cava, in which blood flow through the vena cava was completely obstructed.

In the mid-1970's, the Kimray-Greenfield (KG) vena cava filter was introduced. The original KG filter is conical in shape and is composed of six stainless steel wires equally spaced with its apex cephalad. Although the filter was originally placed using a local cutdown of the jugular or femoral vein, it was later adapted to be inserted percutaneously. The KG filter is designed to capture clots 7 mm or greater in diameter, holding the clots in the infrarenal vena cava until the body's own lytic system dissolves the clot. The principal drawbacks of the KG filter are the possibility of tilting and filter migration, often related to a failure to open, or untimely ejection of the filter from the introducer.

Subsequent versions of the so-called Greenfield filter were developed to reduce the size of the introducer catheter to facilitate percutaneous introduction. Other vena cava filters were introduced in the United States in the late 1980s, including the Vena Tech—LGM vena cava filter, the Bird's Nest vena cava filter, and the Simon-Nitinol vena cava filter. The Vena Tech—LGM filter is a conical filter made from the PHYNOX alloy, with longitudinal stabilizing legs in addition to the intraluminal cone. The Bird's Nest filter is a "nest" of stainless steel wire which is wound into the vena cava, while the Simon Nitinol filter is a two-stage filter made from nickel-titanium alloy with a conical lower section and a petal-shaped upper section. All of these devices are permanent implants which cannot be removed from the body without a major surgical intervention.

Among numerous vena cava filters introduced in Europe but never brought to the United States was the optimal central trapping (OPCETRA) filter. The OPCETRA filter has two main parts: a main basket with ten, long stainless steel wire arms and a distal basket with five, short stainless steel wire arms. This design gives the filter an hourglass shape which provides a self-orienting structure for the filter within the lumen of a blood vessel. The OPCETRA filter was also a permanently implanted vena cava filter.

All of the above-identified vena cava filters are inserted into the body by passing the filter through a catheter to the site of deployment in the infrarenal inferior vena cava. After ejection from the catheter, these filters open or are manually deployed until the filter anchoring elements engage the vessel wall. These filters often have hooks or some other means by which the filter becomes fixed permanently to the vessel wall.

For an important subset of patients, in particular young trauma patients and patients undergoing total hip or knee replacement surgery, the risk of embolism is short-term and limited to a definable period of time. Because of the long-term risks associated with implantation of a permanent blood filter, including venous stasis due to caval occlusion and its related complications, patients whose risk period is limited are not considered good candidates for permanent blood filters. The search for an appropriate temporary therapy for such patients lead to the development of temporary, tethered removable filters.

Tethered temporary filters are attached to a catheter and are implanted in the infrarenal vena cava with the tethering catheter extending out of the puncture site in the neck or groin, or buried subcutaneously within the soft tissues in the patient's neck. The tether remains coupled to the filter after deployment. The tether is then used to retrieve the filter. The potential for septic complications associated with the tethering catheter exiting the -neck or groin require removal of such devices within fourteen days of placement. Risk periods for embolism in such patients, however, can extend up to twenty-one weeks.

Temporary retrievable filters which are not attached to a tethering catheter have a construction similar to some versions of permanent filters. A hook or similar grasping structure is provided to allow a snare to engage the filter during the retrieval procedure. The filter in its entirety is then retrieved using a snare by drawing it into a catheter. However, to ensure the filter does not migrate within the vessel, barbs, anchors or similar structures must be used to engage the filter with the interior wall of the vessel for retaining it in place. These anchors make removal without injuring the vessel difficult. Moreover, after a relatively short period of time the portion of the filter legs in contact with the vessel wall are incorporated by endothelial tissue making retrieval difficult or impossible.

More recently, it has been proposed to provide a removable filter in two parts. An anchoring part of the filter engages the vessel walls, and become incorporated by endothelial tissue. A filter part is releasably coupled to the anchoring part. After the risk of embolism has passed, the filter part may be retrieved using a snare and catheter.

Thus, there is a need for a temporary, convertible blood filter that can be inserted into a vessel to treat vascular disease. Additionally, there is a need for a temporary, convertible blood filter to catch and retain biological debris during procedures such as endarterectomy, angioplasty, or atherectomy, yet be openable to fully restore vessel patency following the treatment.

SUMMARY OF THE INVENTION

The invention provides a filter arranged to be disposed within a blood vessel. The filter includes intraluminal filter elements and is convertible from a filter configuration to an open, stent-like configuration.

The invention also provides a method of treating embolism and atherosclerotic disease using a filter constructed in accordance with the invention.

In a preferred embodiment, the filter device includes a plurality of elements formed into a single cone or dual cone filter structure. A retainer secures the elements in an intraluminal filter configuration upon initial deployment within a vessel. The retainer is then either self-releasing or removable to permit the legs to expand from the filter configuration into what may generally be described as an open or stent-like configuration substantially, totally reopening the lumen.

To maintain stability within the lumen, superior and/or inferior ends of the filter can be formed with a small barb or hook that engages the interior wall of the vessel.

A single cone filter in accordance with the invention includes a plurality of intraluminal filter elements, the superior ends of which are joined by a releasable retainer. In one preferred embodiment, a filter web extends between the plurality of intraluminal elements. In another preferred embodiment, the single cone filter has filter legs which are constrained in the filter configuration. In yet another preferred embodiment, a spring member couples to the legs of the single cone filter to urge them radially outward and revert the filter to an open or stent-like configuration. When in the open configuration, the lumen is substantially unobstructed by the filter.

A dual cone filter in accordance with a preferred embodiment of the invention has intraluminal filter elements joined by a releasable retainer at a location between their superior and inferior ends. In one embodiment, a filter web extends between the intraluminal filter elements. This dual cone shape advantageously improves the self-orienting mechanism of the filter. A spring may join the legs to urge them from the dual cone or hourglass shape into a stent-like configuration upon release of the retainer. Alternatively, the legs may be formed to provide the restoring force.

In still another embodiment, the filter device has intraluminal elements made of a biodegradable material.

In yet another embodiment, the filter device has a releasable retainer joining both ends of the of the intraluminal elements to create a basket-like configuration. The retainer may be self-releasing or removable to permit the intraluminal filter elements to expand from a basket-like configuration into a single cone configuration and subsequently into what may generally be described as an open or stent-like configuration.

BRIEF DESCRIPTION OF THE DRAWINGS

The invention will be described with reference to the following detailed description of several preferred embodiments with reference to the drawings wherein like reference numerals are used to represent like elements, and in which:

FIG. 1 is a side view of a filter in a filter configuration within a blood vessel and having a dual cone structure in accordance with a preferred embodiment of the invention;

FIG. 2 is a view of an intraluminal filter element of the filter shown in FIG. 1 shown in an open configuration;

FIG. 3 is a detailed view of the small barb or hook on the end of the intraluminal filter element of FIG. 1;

FIG. 4 is a cross-section view taken along line 4—4 of FIG. 3;

FIG. 5 is a view of the mesh of wires forming the filter illustrated in FIG. 1;

FIG. 6 is a side view of the filter illustrated in FIG. 1 and further shown in an open, stent-like configuration;

FIG. 7 is a side view of a filter similar to that shown in FIG. 1 and illustrating a releasable retainer restraining the plurality of intraluminal filter elements in a filter configuration at a location between the superior and inferior ends of the elements;

FIG. 8 is an bottom view of the filter shown in FIG. 6;

FIG. 9 is an enlarged side view of a actively releasable retainer that may be used with the filter illustrated in FIG. 1;

FIG. 10 is a cross-section view taken along line 10—10 of FIG. 9;

FIG. 11 is a detailed view of the intraluminal filter elements and tubular apertures of FIG. 10;

FIG. 12 is a side view of a single cone filter in a filter configuration, the filter including axially extending orientation members;

FIG. 13 is a side view of an actively releasable retainer with a hook that may be used with the filter shown in FIG. 12;

FIG. 14 is a side view of a passively releasable retainer that may be used with the filter shown in FIG. 12;

FIG. 15 is a top cross-sectional view of the restrained intraluminal filter elements contained within the releasable retainer shown in FIG. 13;

FIG. 16 is a top cross-sectional view of the restrained intraluminal filter elements contained within the releasable retainer shown in FIG. 14;

FIG. 17 is a cross-sectional view taken along line 17—17 or FIG. 12;

FIG. 18 is a top view of the filter shown in FIG. 12 in an open, stent-like configuration;

FIG. 19 is a side view of a filter in a filter configuration having axially extending orientation members;

FIG. 20 is a cross-sectional view taken along line 20—20 or FIG. 19;

FIG. 21 is a top view of the filter shown in FIG. 19 in an open, stent-like configuration;

FIG. 22 is a side view of a filter in a filter configuration having axially extending orientation members;

FIG. 23 is a side view of the filter shown in FIG. 22 in an open, stent-like configuration;

FIG. 24 is a side view of a filter in a filter configuration having a plurality of intraluminal filter elements that include a corrugated structure;

FIG. 25 is a cross-sectional view taken along line 25—25 or FIG. 24;

FIG. 26 is a top view of the filter shown in FIG. 24 in an open, stent-like configuration;

FIG. 27 is a side view of a filter in a filter configuration with a plurality of intraluminal filter elements having axially extending orientation members;

FIG. 28 is a side view of a filter in a filter configuration with adjacent intraluminal filter elements joined by axially extending orientation members;

FIG. 29 is a side view of a filter in a filter configuration having adjacent intraluminal filter elements joined by a wire mesh and having axially extending orientation members;

FIG. 34 is a side view of a filter having two retainers which form a basket-type filter structure;

FIG. 35 is a side view of the filter in FIG. 34 in a single cone configuration;

FIG. 36 is a side view of the filter in FIG. 34 in an open, stent-like configuration;

FIG. 37 is a side view of a filter in a filter configuration within a blood vessel and having a dual cone structure in accordance with a preferred embodiment of the invention;

FIG. 38 is a side view of a filter in a filter configuration having adjacent intraluminal filter elements joined by a filter web and having axially extending orientation members;

FIG. 39 is a side view of an actively releasable retainer that may used with the filter shown in FIG. 38;

FIG. 39A is a cross-section view of an actively releasable retainer similar to the retainer shown in FIG. 10;

FIG. 40 is a top view of the intraluminal filter elements connected by the filter web shown in FIG. 38 in a closed, filter configuration;

DESCRIPTION OF THE PREFERRED EMBODIMENTS

Figure 30:
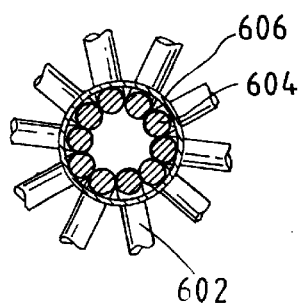
FIG. 30 is a top view of the filter shown in FIG. 29.

Referring generally to FIGS. 1–11, and particularly to FIG. 1, a dual cone blood clot filtration device (filter) 10 in a filter configuration includes a plurality of intraluminal filter elements (filter legs) 12, which may be formed using a suitable wire. As used herein, the term "filter configuration" is used to refer to a filter according to the invention where the intraluminal filter elements are joined by a releasable retainer so as to form a filter structure within the lumen. The term "open configuration" or "stent-like configuration" is used to refer to a filter according to the invention where the releasable retainer has been removed, and the intraluminal filter elements are disposed substantially adjacent an interior wall of the lumen.

With continued reference then to FIG. 1, the filter legs 12 each have a blunted superior end 16 and inferior end 18. Superior and inferior are used in their ordinary sense to refer to the filter's position within the body. The superior ends 16 are positioned upstream relative to blood flow, and the inferior ends 18 are positioned downstream relative to blood flow. The direction of blood flow is indicated in FIG. 1 by the arrow 20. The filter legs 12 are joined by a releasable retainer 22 at some location between the superior ends 16 and the inferior ends 18. In FIG. 1, the releasable retainer 22 secures the filter legs 12 in a dual cone filter configuration. The filter 10 may have a first spring 24 adjacent the superior ends 16 to urge them radially outwardly and a second spring 26 adjacent the inferior ends 18 to likewise urge them radially outward. Alternatively, the filter 10 may have a plurality of annular, horizontal members joining the filter legs 12. The releasable retainer 22 retains the filter legs 12 in the intraluminal dual cone filter configuration, e.g., resists the force exerted on the filter legs 12 by the first spring 24 and the second spring 26. The first spring 24 and the second spring 26 are each shown as an expanding annular spring, however, alternative spring configurations may be used, and several are described in connection with alternate preferred embodiments of the invention described below.

The filter 10 in FIG. 1 is shown inserted into a blood vessel 28 by a physician using the commonly practiced Seldinger technique. For percutaneous insertion of the filter 10, a vein is punctured with a needle, and a guidewire is advanced into the blood vessel 28 through the needle beyond the desired implantation site. A catheter consisting of an inner, dilating cannula within an outer sheath, up to 14 French in diameter, is then advanced into the vein, over the guidewire. When the desired implantation site is reached, the inner dilating cannula and guidewire are removed, leaving the sheath behind. The sheath acts as a conduit to permit the insertion of the filter. The filter 10, in a collapsed configuration, is introduced into the sheath and advanced to the implantation site. Once the filter 10 is in an appropriate position, the filter 10 is pushed out of the sheath or uncovered using a pushing catheter. Upon discharge, the filter legs 12 open and engage the interior wall of the blood vessel 28.

The filter legs 12 may be a flexible wire and, in one preferred embodiment, the wires are metallic and round. In such an embodiment, the wires are preferably a radiopaque and non-ferromagnetic metal which has been certified for use in permanently implanted medical devices by the International Standards Organization (ISO). The wires may, in particular, be a high cobalt, low ferrous alloy, such as that known as and sold under the registered trademarks of "PHYNOX" or "ELGILOY" which may have the composition, by weight percent: cobalt 42%, chromium 21.5%, nickel 18%, iron 8.85%, molybdenum 7.5%, manganese 2% with the balance made up of carbon and beryllium having a maximum of 0.15% carbon and 0.001% beryllium. The wires may also be composed of 316L stainless steel or alloys of nickel and titanium known to be shape-memory metals which are sold and manufactured under the trademark "NITINOL" or an alloy of tantalum. Filter devices 10 constructed from metals will preferably withstand twelve million respiratory cycles without mechanical failure and will be non-thrombogenic.

FIG. 2 shows a single filter leg 12 of the filter 10. The filter 10 and each filter leg 12 are constructed so as to eliminate the possibility of entrapping a guide wire during insertion of the filter 10 into the lumen of a blood vessel. When not being restrained by the releasable retainer 22, each filter leg 12 is relatively straight, running parallel to the axis of the vessel wall 28. Each blunted superior end 16 and inferior end 18 end is flattened and has a small hook or barb 32, best seen in FIG. 3 and FIG. 4, that engages the interior wall of the blood vessel 28, which retain the filter 10 at a desired position within the blood vessel 28. Each filter leg 12 also includes a partially corrugated portion 34. Within a relatively short period of time after implantation, the small hooks or barbs 32 on the superior ends 16 and inferior ends 18 of the filter legs 12, which are in contact with the interior wall of the vessel 28, become permanently connected with the interior wall of the blood vessel 28. The corrugated portion 34 permits outward expansion of the filter leg 12 after release of the releasable retainer 22 without displacement of the superior end 16 or the inferior end 18 as the filter is converted to the stent-like configuration. This arrangement of the filter leg 12 prevents ripping or tearing of the interior wall of the blood vessel 28 upon opening of the filter 10 from the filter configuration shown in FIG. 1 to the open, stent-like configuration shown in FIG. 6. If the filter leg 12 did not include corrugated portion 34 upon release of the releasable retainer 22 and as the filter leg 12 tries to regain its original substantially straight shape, and with each superior end 16 and inferior end 18 engaging the blood vessel 28, this movement of the filter leg 12 may cause the superior end 16 and inferior end 18 to be pulled away from the interior wall of the vessel 28 resulting in injury to the vessel wall.

FIG. 5 shows a plurality of filter legs 12 joined by horizontal connecting members 36 such as by laser welding. Alternatively, a mesh of wires 38 may be formed by the cutting application of a laser micro machining tool. In FIG. 6, the mesh of wires 38 is formed into a stent-like, cylindrical configuration when the ends of the mesh of wires 38 are permanently laser welded together. In a preferred embodiment, the filtration device 10 must be openable to a diameter of not less than "d", preferably about 3.0 cm, yet collapsible to a diameter of less than 12F (4.0 mm) for percutaneous delivery via a catheter introducer system. In a preferred embodiment, the filtration device will be of length "l", preferably about 6–7 cm. As mentioned, the dual cone filter device 10 is self-anchoring on the interior of the vessel wall 28 because of the small hook or barb 32 located on the superior ends 16 and inferior ends 18, yet the blood filter device 10 will have sufficient longitudinal flexibility to pass through fifty-five (55) degrees of angulation and will not substantially distort the vessel after deployment.

In a preferred embodiment of the filter device 110, the dual cone filter configuration converts into an open or stent-like configuration by actively removing the releasable retainer 22. As depicted in FIG. 9, the releasable retainer 40 has a hook 42 with which it can be captured by a snare or other capturing device and pulled through a catheter for removal from the body. In this embodiment, the releasable retainer 40 is cylindrical having axially extending tubular apertures 44 extending its length into which the filter legs 12 are slidably secured until removal of the retainer 40. The releasable retainer 40 joins the filter legs 12 to form the conical filter configuration, FIG, 10 shows a cross-section of the releasable retainer 40 with the filter legs 12 secured within the apertures 44. FIG. 11 is an enlargement of the cross-sectional view of the filter leg 12 within the tubular aperture 44 of the releasable retainer 40. The diameter of the filter leg 12 is less than the diameter of the tubular aperture 44 which enables the filter leg to be slidably released from the releasable retainer 40 when the retainer 40 is snared. It will be appreciated that this construction of the filter 10 offers the possibility of providing a permanent filter, i.e., by leaving the releasable retainer 40 in place, or converting the filter 10 to the-open configuration, and hence, substantially completely reopening the lumen by removing the releasable retainer 40.

Referring again to FIG. 1, the releasable retainer 22 may comprise a band of biodegradable material. Examples of such materials are polylactic acid material or polyglycolic acid suture material commonly used. The advantage of making the releasable retainer 22 from a biodegradable material is that over time the releasable retainer 22 will sufficiently degrade so as to permit the filter legs 12 to move to the open configuration. Thus, the filter device 10 passively converts from a filter configuration to a stent-like configuration. Advantageously, this conversion occurs without a subsequent invasive surgical procedure.

With reference now to FIG. 12, an alternate embodiment of the invention is shown in a single cone filtration device (filter) 100. The filtration device 100 may again be inserted percutaneously into the body using the aforementioned Seldinger technique or any other commonly practiced and federally approved method of insertion.

FIG. 12 shows the single cone filtration device 100 in its expanded position and having a plurality of intraluminal filter elements (filter legs) 102. The filter-legs 102 are a flexible wire and, in one preferred embodiment, the wires are metallic and may be round or flattened wire. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals described with respect to filter 10. In the filter 100 shown in FIG. 12, the filter legs 102 are made of a flattened wire. Each leg 102 has a blunted superior end 104, as discussed in the aforementioned paragraphs describing the superior and inferior positioning within the body, and has a small hook or barb 32 as seen in FIG. 3 and FIG. 4.

The filter 100 has a releasable retainer 106 that joins the superior ends 104 of the filter legs 102 forming a single, conical filter configuration as shown in FIG. 12. In one preferred embodiment, the retainer 106 is rounded or cap-shaped, however alternative retainer configurations could be used. Two preferred releasable filter embodiments are shown in FIG. 13 and FIG. 14. In the embodiment depicted in FIG. 13, the cap-shaped releasable retainer 106 includes a hook 107 which allows the retainer 106 to be actively removed at any time. The hook 107 may be grasped by a snare or other capturing device and the releasable retainer 106 removed from the body, thereby converting the single cone filter 100 to an open, tubular stent-like configuration. The embodiment shown in FIG. 14 has a annular ring-shaped, releasable retainer 106' which may also be removed using a snare device.

As is seen in FIGS. 15 and 16, the releasable retainer 106 has a hollow interior for receiving and retaining the blunted superior ends 104 of the filter legs 102. Upon release of the retainer 106, the filter legs 102 are released converting the filter 100 into an open or stent-like configuration. As seen in FIG. 15 and FIG. 16, the interior of the cap-shaped, releasable retainer 106 is hollow and holds the blunted superior ends 104 of the filter legs 102 by frictional engagement.

Referring again to FIG. 12, the releasable retainer 106 may be a band of biodegradable material such as polylactic acid material or polyglycolic acid suture material. Similar advantages as with filter device 10 are gained by making the releasable retainer 22 from a biodegradable material. Namely, the filter device 100 can be made to passively convert from a filter configuration to a stent-like configuration. Advantageously, this conversion occurs without a subsequent invasive surgical procedure.

In FIG. 12, the single cone filter 100 includes axially extending orientation members 110 to ensure centering of the filter in the vessel and to securely engage the filter with the interior wall of the blood vessel 28. Each orientation member 110 appears to be an appendix on each inferior end 112 of each filter leg 102 which folds substantially toward the closed end of the cone 113 and is substantially aligned with an axis "a" of the filter 100. In one embodiment, each orientation member 110 may be welded or otherwise permanently connected the blunted inferior end 112 of each filter leg 102. In another embodiment, the orientation members 110 may be formed from the same wire as the filter legs 102 by forming the wire so that an acute angle is created between the filter leg portion of the wire 102 and the orientation member portion of the wire 110. Each axially extending orientation member 110 may have one or more small hook or barbs 32 located along the length of the leg 110 for engaging the interior wall of the vessel to maintain the stability and positioning of the filter 100.

As seen in FIG. 12, the filter 100 may have a spring 114 adjacent the superior ends 104 to urge them radially outward, thereby reverting the filter 100 to its stent-like configuration. The spring force required to urge the filter legs 102 to the open configuration, however, is most preferably provided by the formation of the legs themselves in combination with the respective orientation member 110. The releasable retainer 106 resists the force exerted in the legs 102 by either the spring 114, or the energy stored in the filter leg 102 itself, to retain the filtration device 100 in the single cone filter configuration. In a configuration of filter 100 not including a spring 114, an additional member may be provided to join and retain the legs together.

Referring now to FIG. 19, another embodiment of the invention is shown in a single cone filtration device (filter) 200. The filter 200 may be inserted percutaneously into the body using the aforementioned Seldinger technique or by any other commonly practiced and federally approved method of insertion.

FIG. 19 shows the filter 200 in its expanded position having a plurality of intraluminal elements (filter legs) 202. In this embodiment, the filter legs 202 are a flexible wire and may be metallic and round. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. Each filter leg 202 has a blunted superior end 204, and has a small hook or barb 32 as seen in FIG. 3 and FIG. 4.

The filter 200. includes a releasable retainer 206 that joins the superior ends 204 of the filter legs 202 forming a single, conical filter configuration as shown in FIG. 19. In one preferred embodiment, the releasable retainer 206 is rounded or cap-shaped, however alternative retainer configurations could be used. Two preferred releasable retainers are releasable retainers 106 and 106' described above in connection with FIG. 13 and FIG. 14. Equally preferred is the use of a biodegradable retainer as discussed above. Upon release of the retainer 206, either actively with a snaring or other capturing device or passively after sufficient degradation of the biodegradable material, the filter legs 202 are released converting the filter 200 into an open or stent-like configuration.

In FIG. 19, the single cone filter 200 includes axially extending orientation members 208 to ensure centering of the filter in the vessel and to securely engage the filter with the interior wall of the blood vessel 28. Each orientation member 208 appears to be an appendix on the each inferior end 210 of each filter leg 202 which folds substantially backwards toward the tip or closed end of the cone 211. In one embodiment, each orientation member 208 may be welded or otherwise permanently connected to the blunted inferior end 210 of each filter leg 202. In another embodiment, the orientation members 208 may be formed from the same wire as the filter legs 202 by forming the wire so that an acute angle is created between the filter leg portion of the wire 202 and the orientation member portion of the wire 208. Neighboring or adjacent orientation members 208 are joined creating a wishbone-like configuration. Such a configuration assists in maintaining filter stability within the lumen. Each axially extending orientation member 208 may have one or more small hook or barbs 32 located along the length of the leg 208 for engaging the interior wall of the vessel to maintain the stability and positioning of the filter 200. In FIG. 19, the single cone filtration device 200 may have a spring 212 adjacent the superior ends 204 to urge them radially outward. Alternatively, and more preferably, the configuration of the filter legs 202 themselves in conjunction with the respective orientation member 208 provides the energy to urge the filter legs 202 to the open configuration.

The releasable retainer 206 resists the force exerted in the legs 202 by either the spring 212 or the filter legs themselves, to retain the filtration device 200 in the single cone filter configuration. FIG. 20 shows in cross-sectional view the spring 212 attached to and joining the filter legs 202 where the releasable retainer 206 still retains the legs keeping them in a conical configuration. FIG. 21 shows a cross-sectional view of the spring 212 urging the legs radially outwardly into an open and stent-like configuration when the releasable retainer 206 is removed. The small hook 32 on each blunted superior end 204 engages the wall of the vessel for securely fixing the expanded filter within the blood vessel.

Referring now to FIG. 22, in still another alternate preferred embodiment, the filtration device is a single cone filtration device 300. The filtration device 300 may be inserted percutaneously into the body using the aforementioned Seldinger technique or any other commonly practiced and federally approved method of insertion not listed herein.

FIG. 22 shows the single cone filtration device 300 in its expanded position having a plurality of filter legs 302. The legs 302 are a flexible wire and, in one preferred embodiment, the wires are metallic and round. In another embodiment, the wires may be flattened. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. As shown in FIG. 22, each neighboring or adjacent filter leg 302 is joined at its superior end 304. The filter 300 includes a releasable retainer 306 that joins the superior ends 304 of the filter legs 302 forming a single, conical filter configuration as shown in FIG. 22. In one preferred embodiment, the retainer 306 is rounded or cap-shaped, however alternative retainer configurations could be used as discussed above. Upon release of the retainer 306, either actively with a snaring or other capturing device or passively after sufficient degradation of the biodegradable retainer, the filter legs 302 are released converting the filter 300 into an open or stent-like configuration.

In FIG. 22, the single cone filter 300 includes axially extending orientation members 308 to ensure centering of the filter in the vessel and to securely engage the filter with the interior wall of the blood vessel 28. Each orientation member 308 appears to be an appendix on the each inferior end 310 of each filter leg 302 which folds substantially backwards toward the tip or closed end of the cone 311 and is substantially aligned with an axis "a" of the filter 300. In one embodiment, each orientation member 308 may be welded or otherwise permanently connected to the blunted inferior end 310 of each filter leg 302. In another embodiment, the orientation members 308 may be formed from the same wire as the filter legs 302 by forming the wire so that an acute angle is created between the filter leg portion of the wire 302 and the orientation member portion of the wire 308. Each axially extending orientation member 308 may have one or more small hook or barb 32 located along the length of the orientation member 308 for engaging the interior wall of the vessel to maintain the stability and positioning of the filter 300. Preferably the force necessary to move the filter legs 302 is provide by the configuration of the filter legs 302 in conjunction with the orientation members 308. However, in FIG. 22, the single cone filtration device 300 may have a spring 312 adjacent the superior ends 304 to restore the filter to its stent-like configuration by urging the filter legs 302 radially outward. The releasable retainer 306 resists the force attempting to return the filter legs 302 to the open configuration and retains the filtration device 300 in the single cone filter configuration. FIG. 23 shows the spring 312 urging the legs 302 radially outwardly into an open and stent-like configuration after the releasable retainer 306 has been removed. The small hook 32 of each blunted superior end 304 engages the interior wall of the vessel 28 to securely hold the converted filter against the wall of the vessel 28.

Referring to FIG. 24, in another alternate embodiment, the filtration device is a single cone filtration device 400. The filtration device 400 may be inserted percutaneously into the body using the aforementioned Seldinger technique or any other commonly practiced and federally approved method of insertion not listed herein.

FIG. 24 shows the single cone filtration device 400 in its expanded position having a plurality of filter legs 402. The legs 402 are a flexible wire and, in one preferred embodiment, the wires are metallic and round. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. The wire filter legs 402 are corrugated to enhance filtering of blot clots. Each leg 402 has a blunted superior end 404, as discussed in the aforementioned paragraphs describing the superior and inferior positioning within the body, and has a small hook or barb 32 as seen in FIG. 3 and FIG. 4. The filter 400 includes a releasable retainer 406 that joins the superior ends 404 of the filter legs 402 forming a single, conical filter configuration as shown in FIG. 24. In one preferred embodiment, the retainer 406 is rounded or cap-shaped, however alternative retainer configurations could be used as discussed above. Upon release of the retainer 406, either actively with a snaring or other capturing device or passively after sufficient degradation of the biodegradable retainer, the filter legs 402 are released converting the filter 400 into an open or stent-like configuration.

In FIG. 24, the single cone filter 400 may be configured to include axially extending orientation members (not depicted) to ensure centering of the filter in the vessel and to securely engage the filter with the interior wall of the blood vessel 28. Each orientation member appears to be an appendix on the each inferior end 410 of each filter leg 402 which folds substantially toward the closed end of the cone 411. In one embodiment, each orientation member may be welded or otherwise permanently connected to the blunted inferior end 410 of each filter leg 402. In another embodiment, the orientation members may be formed from the same wire as the filter legs 402 by forming the wire so that an acute angle is created between the filter leg portion of the wire 402 and the orientation member portion of the wire, Each axially extending orientation member may have one or more small hook or barbs 32 located along the length of the leg for engaging the interior wall of the vessel to maintain the stability and positioning of the filter 400. The configuration of the legs 402 and orientation members may provide the force necessary to revert the filter legs 402 to the open configuration. In FIG. 24, the single cone filtration device 400 may have a spring 412 adjacent the superior ends 404 to revert the filter legs 402 to the open configuration. The releasable retainer 406 resists the force exerted in the legs 402 to retain the filtration device 400 in the single cone filter configuration. FIG. 25 shows a cross-sectional view of the spring 412 attached to and joining the filter legs 402 where the releasable retainer 406 still retains the legs keeping them in a conical configuration. FIG. 26 shows a cross-sectional view of the spring 412 urging the legs radially outwardly thereby reverting them into an open and stent-like configuration when the releasable retainer 406 is removed. The small hook 32 on each blunted superior end 404 engages the wall of the vessel for securely fixing the expanded filter within the blood vessel.

In certain preferred embodiments of a filter device described above a spring in not needed to urge the filter legs radially outwardly to restore the filter to its open configuration. In FIG. 27, the single cone filter 500 is formed substantially the same way as the single cone filter 100 shown in FIG. 12. The filter legs, releasable retainer, and orientation members are in accordance with the foregoing discussion associated with single cone filter 100. In FIG. 28, the single cone filter 600 is formed substantially the same way as single cone filter 200 shown in FIG. 19. The filter legs, releasable retainer, and orientation members are in accordance with the discussion associated with single cone filter 200. When the releasable retainer is removed from the single cone filter 500 and single cone filter 600, the filters are self-opening. Each filter leg and orientation member of filter 500 and filter 600 is formed from a single wire. The wire is bent forming a hair-pin configuration. The energy stored in wires causes the filter legs to self-open upon release of the retainer and thereby create an open or stent-like configuration.

In FIG. 29, the single cone filter 700 is constructed similarly to the aforementioned blood filters. In filter 700, each neighboring or adjacent filter legs is connected at is superior end and each neighboring or adjacent orientation member is connected. Thus, filter 700 is formed from one continuous piece of wire that has been formed into a stent-like configuration and then retained by a releasable retainer in a filter configuration. If the wire of filter 700 were broken at one point and the wire laid flat, the shape of the wire may appear similar to a sinusoidal wave. In filter 700, between each adjacent and connected filter leg, the filter legs may have a mesh of wires to enhance filtering during embolization. The meshed wires 703 are seen in FIG. 29.

Figure 31:
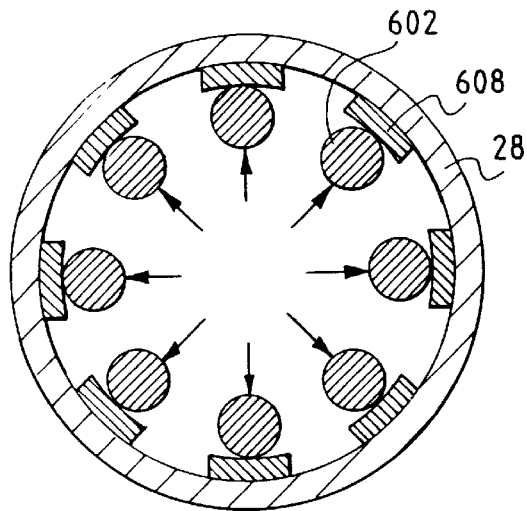
FIG. 31 is a top view of the filter shown in FIG. 29 in an open, stent-like configuration.

In accordance with the preferred embodiments, the filter legs of filters 500, 600 and 700 are retained in a releasable retainer while in the single cone configuration. The releasable retainer resists the force restoring the filter legs to the open configuration and thus retains the filter legs in the single cone filter configuration. FIG. 30 shows a cross-sectional view of the filter legs of filters 500, 600 and 700 joined or retained by a releasable retainer. FIG. 31 shows a cross-sectional view of the filter legs of filters 500, 600 and 700 expanding radially outwardly into an open and stent-like configuration when the releasable retainer is removed. A small hook 32 on each blunted superior end of each filter leg engages the wall of the vessel to securely fix the expanded filter within the blood vessel. In this expanded position, the interior of the blood vessel lumen is open for the free-flow of blood.

Figure 32:
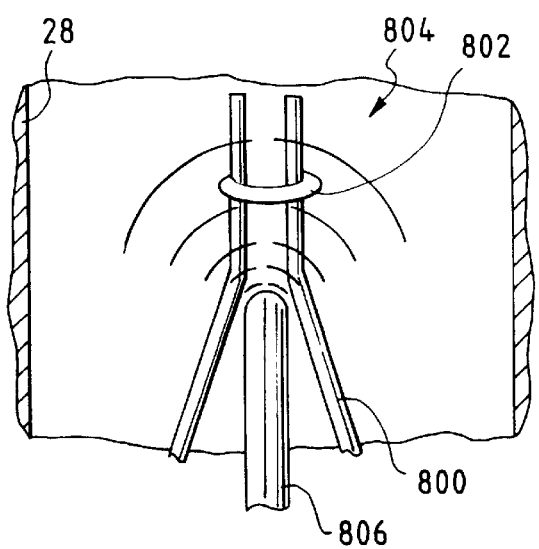
FIG. 32 is a side view of a device inserted into the lumen near a filter in a filter configuration in accordance with the invention for releasing the retainer.
Figure 33:
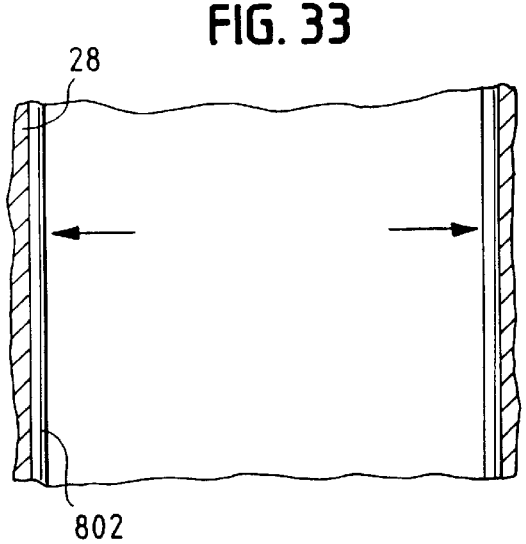
FIG. 33 is a side view of the filter shown in FIG. 32 in an open, stent-like configuration.

As mentioned previously, the releasable retainer in each of the aforementioned embodiments can be actively or passively removed. FIG. 32 shows filter legs 800 that are restrained by a releasable retainer 802 in the form of a band. The filter legs 800 form a conical filter configuration. In FIG. 32, the releasable retainer 802 is a band the engages each of the filter legs. This retainer 802 is generally biologically stabile, i.e., does not degrade within the body, until being exposed to an energy stimulus or a chemical stimulus. The waves 804 shown in FIG. 32 represent an energy stimulus. An emitter 806 is depicted by the rod-like structure in FIG. 32, but is not limited to such a structure configuration. The waves 804 given off by the emitter 806 may be an ultrasonic energy or an electrical current. In another embodiment, the emitter 806 may release waves 804 of a chemical stimulus that breaks or dissolves the retaining band 800. Preferably the band remains structurally stable until it is exposed to the either the mechanical, electrical or chemical stimulus. For example, a polymer material responsive to ultrasound energy to initiate a degradation process is described in U.S. Pat. No. 4,657,543, the disclosure of which is incorporated by reference. In an alternative embodiment, the retainer 802 is a stainless steel material that may be electrolytically disintegrated as is known in the art. After exposure to the energy stimulus, the retainer 802 begins to degrade similar to the above-described biodegradable releasable retainers or otherwise sufficiently structurally weakens so as to permit the release of the filter legs 800. Upon release, as shown in FIG. 33, the filter legs 800 expand to form the an open or stent-like configuration when the retainer 802 degrades as a result of exposure to either an energy stimulus or a chemical stimulus.

In FIG. 34, the basket-type filter 810 is constructed similarly to the aforementioned single cone filters except that the releasable retainer joins both ends of the filter 810. In this embodiment, the releasable retainer may be a first releasable retainer 812 and a second releasable retainer 814. The filter 810 may be inserted percutaneously into the body using the aforementioned Seldinger technique or any other commonly practiced and approved method of insertion. The intraluminal filter elements (filter legs) 811 are a flexible wire and, in one preferred embodiment, may be round or flattened wire. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals described with respect to filter 10. The filter legs 811 are gathered at one end by releasable retainer 812 and at the other end by releasable retainer 814. A filter web 816 extends between the filter legs 811. The filter web 816 may be made of woven metal or may be a plurality individual members extending between the filter legs 811. Because of the symmetric configuration of the basket-type filter 810, the filter 810 does not have designated superior and inferior ends as described previously in connection with the single and dual cone filter configurations. For this reason, the filter 810 may be implanted in the vena cava from above or below. Each retainer 812, 814 of filter 810 includes a hook 813, 815 which allows the respective retainer 812, 814 to be actively removed at any time like the retainer depicted in FIG. 13. The hooks 813, 815 may be grasped by a snare or other capturing device and the retainer 812, 814 removed from the body. As is shown in FIG. 35, the basket-type filter 810 converts to a single cone filter configuration when the inferiorly positioned one of the retainers 812, 814 is removed. When the remaining superiorly positioned one of the retainers 812, 814 is removed, the single cone configuration converts to an open, stent-like configuration as is depicted in FIG. 36. The superior retainer is the one of the retainers positioned upstream relative to blood flow, and the inferior retainer is the other of the retainers positioned downstream relative to blood flow. In alterative embodiments of the invention, the basket-type filter 810 may include biodegradable retainers which, advantageously, allow the conversion to occur without a subsequent invasive surgical procedure. In additional embodiments of the invention, the basket-type filter 810 may include retainers that are releasable upon exposure to a form of mechanical, electrical or chemical stimulus.

In accordance with additional preferred embodiments of the invention, a filter is placed in an artery downstream from the diseased portion of the arterial vessel to prevent large pieces dislodged plaque as well as any other potentially harmful embolic material from occluding smaller vessels. A filter inserted downstream catches plaque dislodged by during the treatment procedure, such as endarterectomy, and retains it until the plaque is removed from the filter by a vacuuming procedure. In addition to catching dislodged plaque, the filters catches harmful blood clots in the bloodstream. Such blood clots may develop as a result of damage to the normal healthy lining of the blood vessel caused by the plaque removal. For example, when blood platelets come into contact with the site of vessel damage, they become activated, adhering to the site and initiate the formation of a blood clot or thrombus. The thrombus may enlarge until it blocks the vessel at the site, or the continued flow of blood past the thrombus may cause it to dislodge. Thromboembolism may have serious consequences for patients suffering from atherosclerosis if the free floating clot, or embolus, completely plugs a smaller vessel as it migrates downstream. Thus, it is desirable to place filters in the bloodstream to catch any potentially harmful pieces of plaque or other embolic material.

Similarly, with balloon angioplasty, plaque may dislodge from the arterial wall and enter the blood stream. As mentioned previously, it would be desirable to catch the plaque in a filter and remove it from the body before a cerebral vascular accident occurs.

With reference to FIG. 37, a filter 820, in accordance with an alternate preferred embodiment of the invention, is shown. The filter 820 has a dual cone configuration and includes a plurality of intraluminal filter elements (filter legs) 822. The filter 820 may be inserted percutaneously into the body using the aforementioned Seldinger technique or any other commonly practiced and approved method of insertion. The filter legs 822 are a flexible wire and, in one preferred embodiment, may be round or flattened wire; The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals described with respect to filter 10. The filter legs 822 each have a blunted superior end 824 and inferior end 826. Superior and inferior are used in their ordinary sense to refer to the filter's position within the body. The superior ends 824 are positioned upstream relative to blood flow, and the inferior ends 826 are positioned downstream relative to blood flow. The direction of blood flow is indicated in FIG. 37 and FIG. 38 by the arrow 828.

In FIG. 37, the filter legs 822 are joined by a releasable retainer 830 at a location between the superior ends 824 and the inferior ends 826. The releasable retainer 830 secures the filter legs 822 in the dual cone configuration. The filter 820 may have a first member 832 adjacent the superior ends 824 and a second member 834 adjacent the inferior ends 826. The first member 832 and the second member 834 support the filter legs 822 radially and axially.

The filter 820 has a filter web 836 extending between the portion of the filter legs 822 that is disposed between the releasable retainer 830 and the inferior ends 826. The filter web 836 is shown only extending between two of the plurality of filter legs 822, but it should be understood that in a preferred embodiment of the invention the filter web 836 may extend between all of the filter legs 822, or some portion of the filter legs 822. The filter web 836 may be made of woven metal or may be a plurality of individual members extending between the filter legs 822. The filter web 836 enhances the effectiveness of the filter 820 to retain pieces of dislodged plaque and thrombotic material.

The releasable retainer 830 retains the filter legs 822 in the intraluminal dual cone filter configuration, e.g., resists the tendency of the filter legs 822 to return to an open configuration. That is, the first member 832 and the second member 834 maintain the relative spacing of the filter legs 822, and in general, retain the filter legs 822 in a cylindrical or stent-like configuration (similar to that of the filter 10 shown in FIG. 6). The releasable retainer 830, by engaging the filter legs 822, restricts the central portion of the filter legs 822 and retains the filter legs 822 in the dual cone filter configuration. By withdrawing the releasable retainer 830 from the filter legs 822, the filter legs 822 are permitted to completely open into the cylindrical configuration. The first member 832 and the second member 834 are each shown as an expanding annular spring; however, one of ordinary skill in the art will appreciate that alternative configurations may be used.

Each of the filter legs 822 of the filter 820 may be constructed similar to the single filter leg 12 of the filter 10 as depicted in FIG. 2. Each blunted superior end 824 and inferior end 826 is flattened and may include a small hook or barb (such as barb 32, best seen in FIG. 3 and FIG. 4) that engages the interior wall of the blood vessel 838. These barbs help secure the filter 820 within the lumen of an arterial blood vessel 838 and resist the pressures of the blood pumping through the arterial system. It is not necessary that each end, 824 and 826, of each filter leg 822 include a barb. Instead, the barbs may be disposed on alternating ends, or may be disposed on preselected ones of the ends. Such an arrangement of the filter 820, with barbs disposed on alternating ends of the filter legs 822, may enhance deployment of the filter into the vessel. In a filter having barbs disposed on the end of each filter leg, it is possible that, as the filter is discharged from the introducer catheter, the barbs of adjoining filter legs may engage the vessel wall before they have expanded to their full radial extension. The result is the filter may not fully deploy. By providing barbs on alternating filter leg ends, or even fewer ends, the tendency for the barbs to improperly engage the vessel is reduced.

Each filter leg 822 may also include a partially corrugated portion along its length (similar to the corrugated portion 34 of the filter 10 illustrated in FIG. 2). Within a relatively short period of time after implantation, the barbs on the superior ends 824 and inferior ends 826 of the filter legs 822, which are in contact with the interior wall of the vessel 838, become permanently connected with the interior wall of the blood vessel 838. The corrugated portion permits outward expansion of the filter leg 822 after release of the releasable retainer 830 without displacement of the superior end 824 or the inferior end 826 as the filter is converted to the stent-like configuration. This arrangement of the filter leg 822 reduces the likelihood of damaging the interior wall of the blood vessel 838 upon opening of the filter 820 from the filter configuration to the open, stent-like configuration.

In a preferred embodiment, the filtration device 820 must be openable to a diameter of not less than "d", about 2–10 mm, and preferably about 4 mm, yet collapsible to a diameter of less than 8F (2.6 mm) for percutaneous delivery via a catheter introducer system. In a preferred embodiment, the filtration device will be of length "l", preferably about 2–10 mm. As mentioned, the dual cone filter device 820 is self-anchoring on the interior of the vessel wall 838 because of the barbs located on the superior ends 824 and inferior ends 826, yet the blood filter device 820 will have sufficient longitudinal flexibility to pass through fifty-five (55) degrees of angulation and will not substantially distort the vessel after deployment.

In a preferred embodiment of the filter device 820, the dual cone filter configuration converts into an open or stent-like configuration by actively removing the releasable retainer 830. This conversion to a stent-like configuration is especially desirable when treating atherosclerotic disease as described above. For example, after a balloon angioplasty procedure, stents are often inserted into the treated region of an artery to keep the lumen open, maintain blood flow and provide a scaffolding for tissue growth.

The releasable retainer 830 may be constructed similar to the retainer 40 depicted in FIG. 9 and include a hook 842 with which it can be captured by a snare or other capturing device and pulled through a catheter for removal from the body. Like the retainer in FIG. 9, the releasable retainer 830 may be cylindrical having axially extending tubular apertures extending its length into which the filter legs 822 are slidably secured until removal of the retainer 830. As shown in FIG. 37, the releasable retainer 830 is a band, for example of suture material, that may be cut and removed via a catheter. Alternatively, the releasable retainer 830 may be a band of biodegradable material. Examples of such materials are polylactic acid material or polyglycolic acid suture material commonly used. The advantage of making the releasable retainer 830 from a biodegradable material is that over time the releasable retainer 830 will sufficiently degrade so as to permit the filter legs 822 to move to the open configuration. Thus, the filter device 820 passively converts from a filter configuration to a stent-like configuration, advantageously occuring without a subsequent invasive surgical procedure.

Referring now to FIG. 38, in accordance with yet another embodiment of the invention, a single cone filtration device (filter) 900 is shown. The filter 900 may be inserted percutaneously into the body using the aforementioned Seldinger technique or by any other commonly practiced and approved method of insertion.

FIG. 38 shows the filter 900 in its expanded position having a plurality of intraluminal elements (filter legs) 902. In this embodiment, the filter legs 902 are constructed from flexible wire that may be metallic and round. The wires are preferably radiopaque, non-thrombogenic, and non-ferromagnetic metal meeting the certifications for permanently implanted medical devices according to the ISO and will preferably be able to withstand twelve million respiratory cycles. In particular, the wire may consist essentially of any of the aforementioned metals.

Each filter leg 902 has a blunted inferior end 904, and each inferior end 904 may be formed to include a barb. Other embodiments of filter 900 may include alternating ends formed with a barb, or each end of selected ones of the filter legs 902 including a barb. The single cone filter illustrated in FIG. 38 may be formed substantially the same way as single cone filter 200. As such, the filter legs 902, and orientation members 906 are formed in accordance with the discussion associated with single cone filter 200.

The filter 900 shown in FIG. 38 has a releasable retainer 908 that joins the superior ends of the filter legs 902 forming a single, conical configuration as shown. In one preferred embodiment, the retainer 908 is rounded or cap-shaped, however alternate retainer configurations could be used. In the embodiment depicted in FIG. 39, the cap-shaped releasable retainer 908 includes a hook 909 which allows the retainer 908 to be actively removed at any time. The hook 909 may be grasped by a snare or other capturing device and the releasable retainer 908 removed from the body, thereby converting the single cone filter 900 to an open, tubular, stent-like configuration. As shown in FIG. 39A, the releasable retainer 908 may be formed to include axially extending tubular apertures 903 into which the filter legs 902 are slidably engaged similar to those shown in connection with retainer 40 of FIG. 9.

When the releasable retainer 908 is removed from the single cone filter 900, the filter is self-opening to an open, stent-like configuration. Each filter leg 902 and orientation member 906 may be formed from a single wire that is formed into a hairpin-like configuration as shown in FIG. 38. Alternatively, all the filter legs 902 and orientation members 906 may be formed from a continuous piece of wire and retained by the releasable retainer 908 in a filter configuration. Upon release of the retainer 908 from the filter, the elastic energy stored in the wire(s) causes the filter legs to self-open and thereby create an open or stent-like configuration.

In accordance with the preferred embodiments of the invention, the filter legs 902 are connected by a filter web 910 that consists of a wire mesh. This filter web enhances the effectiveness of the filter 900 for retaining small pieces of plaque during the treatment of vascular disease. As is best illustrated in FIG. 40, when single cone filter 900 is in the filter configuration the filter web 910 fills the lumen of the blood vessel, contacting the interior wall of the arterial blood vessel 838, to catch migrating pieces of dislodged plaque and thrombotic material in the bloodstream.

Figure 41:
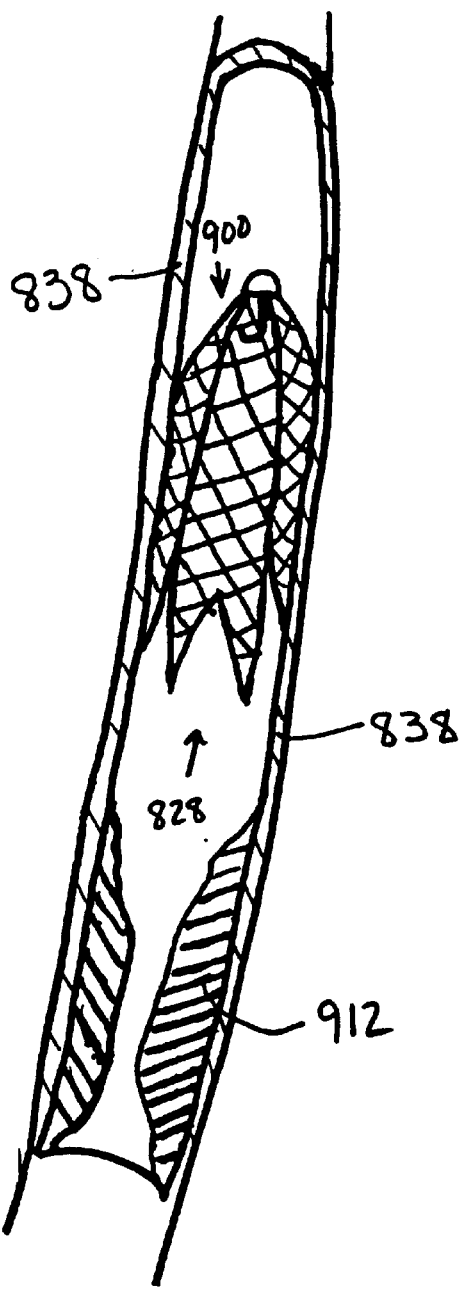
FIG. 41 is a side view of a filter shown in FIG. 38 position superior to the plaque in an arterial blood vessel.
Figure 42:
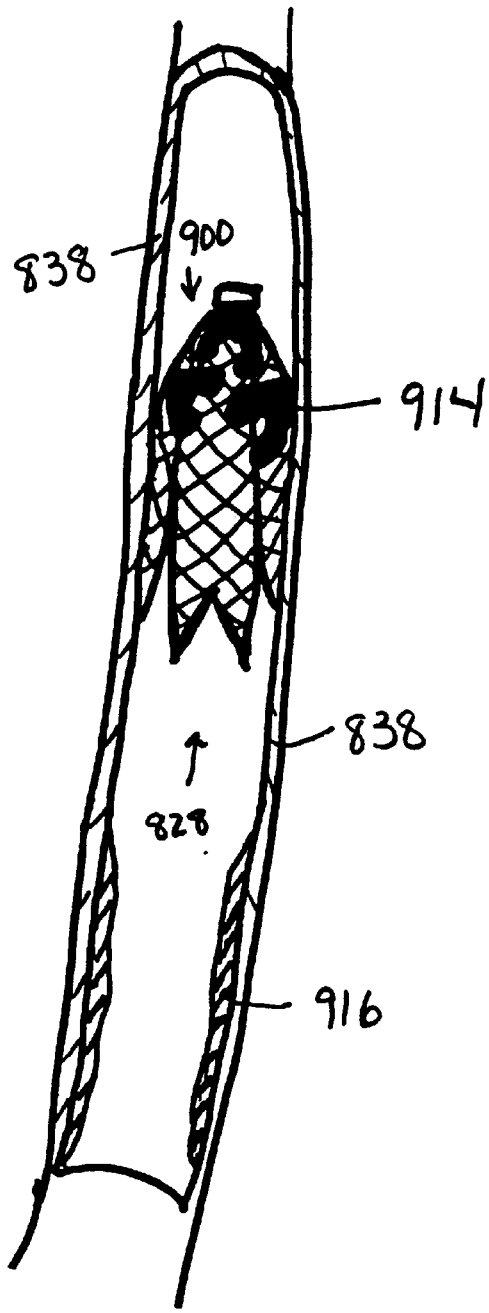
FIG. 42 is a side view of the filter shown in FIG. 38 retaining dislodged plaque and thrombotic material.
Figure 43:
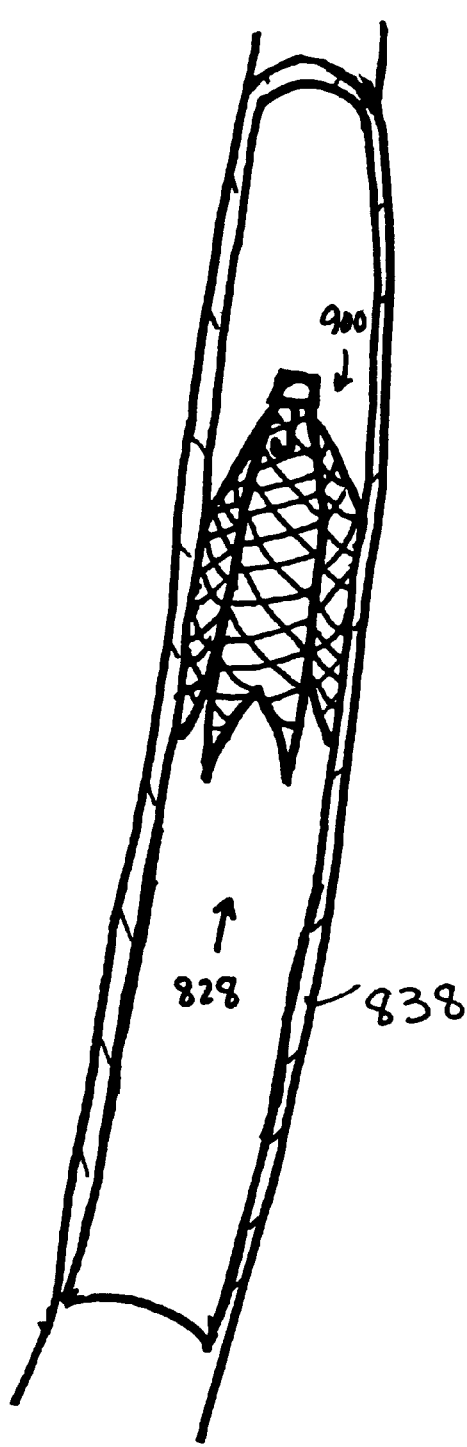
FIG. 43 is a side view of the filter shown in FIG. 41 after plaque has been removed from the filter.
Figure 44:
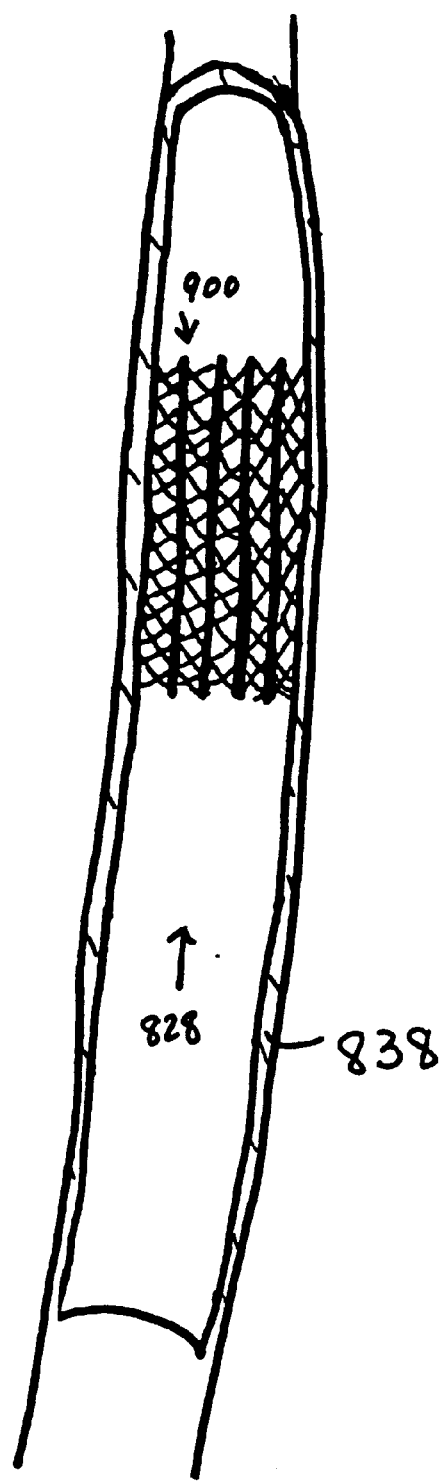
FIG. 44 is a side view of the filter shown in FIG. 41 in an open, stent-like configuration.

In accordance with a method of treating atherosclerotic disease by endarterectomy, balloon angioplasty, atherectomy or other interventional methods, a filter, e.g., a filter 820 or a filter 900, may be inserted into the vessel being treated and downstream, relative to the direction of blood flow (indicated by arrow 828 in FIGS. 41–44), from the area of the vessel being treated. As shown in FIG. 41, a filter 900 may be placed downstream from deposits of atherosclerotic plaque 912 that have accumulated on the interior lining of an arterial blood vessel 838. As shown in FIG. 42, the filter 900 catches harmful debris 914 in the bloodstream including plaque dislodged by the treatment procedure as well as thrombotic material. The filter 900 retains this debris 914 until the debris 914 is removed from the filter 900 by a vacuuming procedure known by one skilled in the art. Some residual atherosclerotic plaque 916 may remain on the interior lining of the arterial blood vessel 838. In FIG. 43, at the completion of the treatment, the residual plaque 916 is removed from the interior lining (traces of plaque may still line the arterial wall yet are not depicted in FIGS. 43 and 44) of the arterial blood vessel 838 and all debris 914 is removed from the filter 900. Finally, as depicted in FIG. 44, the filter 900 may convert to its open, stent-like configuration if of the releasable retainer is removed, either passively or actively as described above in connection with the vena cava filters. The filter 900 in the open, stent-like configuration restores vessel patency, keeps the lumen open and provides a scaffolding for the growth of new tissue on the interior lining of the arterial blood vessel 838. While it is not anticipated that the filter will be left for extended periods in the filter configuration, and instead it is likely the filter will be converted to the open, stent-like configuration shortly after completing the treatment, such methods of treatment utilizing a filter as shown herein are within the scope of the invention.

In an alternate embodiment, any of the aforementioned filters may be made both passively self-opening and entirely biodegradable based upon the materials selected to form the filter structure. The filter itself, and particularly the intraluminal elements (filter legs), the orientation members and the filter web, where necessary, may be formed of a biodegradable material which degrades within the body after a specified period of time. Such materials are biocompatible with the body which means that they are physiologically tolerable. Preferably, such biocompatible materials do not cause undesirable physiological conditions that may result in changes in the structure and function of living tissues in the body. In one preferred embodiment, the filter may be composed essentially of the biodegradable and biocompatible material polylactic acid (pla). An alternate preferred material is the copolymer of L-lactide and .∈.-caprolactone as described in U.S. Pat. No. 5,670,161, the disclosure of which is hereby incorporated by reference. The releasable retainer used in conjunction with the filters composed substantially of biodegradable materials is made of a second biodegradable and biocompatible material. In one preferred embodiment, the releasable retainer is made of the biodegradable material polyglycolic acid (pga). The biodegradable material selected for the filter structure has a degradation rate (d1) preferably slower than a degradation rate (d2) of the biodegradable material selected for the releasable retainer(s). Thus, the releasable retainer(s) will degrade or dissolve first thereby releasing the filter legs and converting the filter into a stent-like configuration. The filter legs then move into contact with the lumen walls and in relatively short period of time are incorporated by endothelial tissue. After a further period of time, i.e., the difference between the filter degradation rate (d1) and the retainer degradation rate (d2), the filter will begin to degrade within the body. A preferred first degradation rate (d1) may be up to one year while a preferred second degradation rate (d2) may be approximately 21 weeks. Advantageously, because of the biodegradable composition of the filter and the retainer, none of the filter materials will remain in the body. Thus, a filter constructed in accordance with this embodiment of the invention may be particularly preferred by surgeon wherein the risk of embolism is transient. It will be further appreciated that the foregoing described biodegradable materials, equivalent materials, and improvements to such materials, suitable for use in forming a filter structure are contemplated to be within the scope of the invention.

The invention has been described in terms of several preferred embodiments. The description of these embodiments should in no way be considered limiting of the broad scope of the invention set forth in the following claims.

I claim:

1. A filter adapted for use in treating vascular disease, the filter comprising:
    a plurality of interconnected intraluminal filter elements, the intraluminal filter elements arranged to be disposed in a filter configuration within a lumen of a blood vessel,
    an untethered releasable retainer joining the intraluminal filter elements in the filter configuration, and
    wherein upon release in vivo of the releasable retainer the intraluminal filter elements convert to an open configuration in the lumen of the blood vessel.

2. The filter of claim 1, further comprising a spring formed integrally with the plurality of intraluminal filter elements.

3. The filter of claim 1, further comprising a filter web interconnecting the filter elements.

4. The filter of claim 3, wherein the filter web extends between each adjacent intraluminal filter element.

5. The filter of claim 3, wherein the filter web is formed integrally with the intraluminal filter elements.

6. The filter of claim 1, further comprising means for releasing the releasable retainer after a predetermined time period.

7. The filter of claim 1, wherein the releasable retainer comprises a biodegradable material.

8. The filter of claim 1, further comprising means for actively releasing the releasable retainer.

9. The filter of claim 1, wherein the releasable retainer comprises a coupling formed with a plurality of catches, each of the catches respectively engaged with one of the plurality of intraluminal filter elements.

10. The filter of claim 1, wherein the releasable retainer comprises a breakable band engaging each of the plurality of intraluminal filter elements.

11. The filter of claim 1, further comprising means for releasing the releasable retainer responsive to an energy stimulus.

12. The filter of claim 1, further comprising means for releasing the releasable retainer responsive to a chemical stimulus.

13. A filter for use in treating vascular disease comprising:
    a plurality of interconnected intraluminal filter elements each having a superior end and an inferior end,
    a plurality of orienting members secured to and extending from respective ones of the intraluminal filter elements,
    a releasable retainer joining the superior ends in a filter configuration the releasable retainer being unsecured by a tethering element, and
    wherein upon release of the releasable retainer the intraluminal filter elements convert to an open configuration.

14. The filter of claim 13, further comprising a plurality of members joined to the intraluminal filter elements to restore the superior ends to an open configuration-upon release of the retainer.

15. The filter of claim 13, further comprising a filter web interconnecting the intraluminal filter elements.

16. The filter of claim 15, where in the filter web extends between each adjacent intraluminal filter element.

17. The filter of claim 15, wherein the filter web is formed integrally with the intraluminal filter elements.

18. The filter of claim 13, wherein each orienting member is formed integrally with a respective intraluminal filter element.

19. The filter of claim 13, wherein each orienting member comprises a portion of the respective intraluminal filter element extending substantially parallel to an axis of filtration.

20. The filter of claim 13, wherein each orienting member comprises an elongate portion of the respective intraluminal filter element extending from the respective superior end and radially outwardly from the retainer.

21. The filter of claim 13, wherein each orienting member comprises a loop extending between the inferior ends of adjacent intraluminal filter elements.

22. The filter of claim 13, wherein the releasable retainer comprises a biodegradable material.

23. The filter of claim 13, further comprising means for actively releasing the releasable retainer.

24. The filter of claim 13, wherein the releasable retainer comprises a coupling formed with a plurality of catches, each of the catches respectively engaged with one of the plurality of intraluminal filter elements.

25. The filter of claim 13, wherein the releasable retainer comprises a breakable band engaging each of the plurality of intraluminal filter elements.

26. The filter of claim 13, further comprising means for releasing the releasable retainer responsive to an energy stimulus.

27. The filter of claim 13, further comprising means for releasing the releasable retainer responsive to a chemical stimulus.

* * * * *

UNITED STATES PATENT AND TRADEMARK OFFICE
CERTIFICATE OF CORRECTION

| | |
|---|---|
| PATENT NO. | : 6,517,559 B1 |
| APPLICATION NO. | : 09/564141 |
| DATED | : February 11, 2003 |
| INVENTOR(S) | : Paul A. O'Connell |

It is certified that error appears in the above-identified patent and that said Letters Patent is hereby corrected as shown below:

Column 20, line 56, please delete the phrase "the releasable retainer being unsecured by a tethering element".

Column 20, line 59, after the term configuration, please insert --, the releasable retainer being unsecured by a tethering element--.

Column 20, line 62, please delete the phrase "configuration-upon" and insert --configuration upon-- therefore.

Signed and Sealed this

Eighth Day of December, 2009

David J. Kappos
*Director of the United States Patent and Trademark Office*